United States Patent
Gonzalez Buenrostro et al.

(10) Patent No.: US 9,758,495 B2
(45) Date of Patent: Sep. 12, 2017

(54) HETEROARYL ACID MORPHOLINONE COMPOUNDS AS MDM2 INHIBITORS FOR THE TREATMENT OF CANCER

(71) Applicant: AMGEN INC., Thousand Oaks, CA (US)

(72) Inventors: Ana Gonzalez Buenrostro, San Mateo, CA (US); Yihong Li, Johns Creek, GA (US); Julio C. Medina, San Carlos, CA (US); Steven H. Olson, Millbrae, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 14/774,645

(22) PCT Filed: Mar. 13, 2014

(86) PCT No.: PCT/US2014/026584
§ 371 (c)(1),
(2) Date: Sep. 10, 2015

(87) PCT Pub. No.: WO2014/151863
PCT Pub. Date: Sep. 25, 2014

(65) Prior Publication Data
US 2016/0039774 A1  Feb. 11, 2016

Related U.S. Application Data

(60) Provisional application No. 61/784,230, filed on Mar. 14, 2013.

(51) Int. Cl.
| | | |
|---|---|---|
| *C07D 265/32* | (2006.01) | |
| *C07D 413/06* | (2006.01) | |
| *C07D 417/06* | (2006.01) | |

(52) U.S. Cl.
CPC ......... *C07D 265/32* (2013.01); *C07D 413/06* (2013.01); *C07D 417/06* (2013.01)

(58) Field of Classification Search
CPC ... C07D 265/32; C07D 413/06; C07D 417/06
See application file for complete search history.

(56) References Cited

U.S. PATENT DOCUMENTS

| | | | |
|---|---|---|---|
| 3,308,121 A | 3/1967 | Gannon et al. | |
| 3,518,236 A | 6/1970 | Hunter | |
| 5,334,720 A | 8/1994 | Schmiesing et al. | |
| 6,620,815 B1 | 9/2003 | Lagu et al. | |
| 6,860,940 B2 | 3/2005 | Segelke et al. | |
| 7,015,041 B2 | 3/2006 | Santarsiero et al. | |
| 7,052,545 B2 | 5/2006 | Quake et al. | |
| 7,195,670 B2 | 3/2007 | Hansen et al. | |
| 7,214,540 B2 | 5/2007 | DeLucas et al. | |
| 7,229,500 B2 | 6/2007 | Haushalter et al. | |
| 7,425,638 B2 | 9/2008 | Haley et al. | |
| 7,776,875 B2 | 8/2010 | Chen et al. | |
| 8,569,341 B2 | 10/2013 | Gribble, Jr. et al. | |
| 8,952,036 B2 | 2/2015 | Rew | |
| 9,296,736 B2 | 3/2016 | Bartberger et al. | |
| 9,376,386 B2 | 6/2016 | Bio et al. | |
| 9,376,425 B2 | 6/2016 | Bartberger et al. | |
| 9,593,129 B2 | 3/2017 | Bartberger et al. | |
| 9,623,018 B2 | 4/2017 | Bio et al. | |
| 2004/0186134 A1 | 9/2004 | O'Connor et al. | |
| 2007/0129416 A1 | 6/2007 | Ding et al. | |
| 2008/0280769 A1 | 11/2008 | Doemling | |
| 2009/0143364 A1 | 6/2009 | Fotouhi et al. | |
| 2009/0163512 A1 | 6/2009 | Chen et al. | |
| 2011/0319378 A1 | 12/2011 | Gribble, Jr. et al. | |
| 2014/0235629 A1 | 8/2014 | Bartberger et al. | |
| 2014/0315895 A1 | 10/2014 | Bartberger et al. | |
| 2014/0364455 A1 | 12/2014 | Bio et al. | |

(Continued)

FOREIGN PATENT DOCUMENTS

| | | |
|---|---|---|
| CN | 102153557 A | 8/2011 |
| DE | 3246148 A1 | 6/1984 |

(Continued)

OTHER PUBLICATIONS

Voskoglou-Nomikos et al., Clinical Cancer Research, vol. 9, 4227-4239.*
ptcl.chem.ox.ac.uk/MSDS structure activity relationship; Jaworska, 1-8, 2004.*
Cancer and Metastasis Reviews (1998), 17(1), 91-106.*
Science (1999), vol. 286, 531-537.*
Notice of Allowance dated Feb. 19, 2016, 2014 for U.S. Appl. No. 14/347,628, filed Mar. 26, 2014, pp. 1-5.
U.S. Appl. No. 15/163,186, filed May 24, 2016, Amgen Inc.
U.S. Appl. No. 15/175,798, filed Jun. 7, 2016, Amgen Inc.
U.S. Appl. No. 15/175,805, filed Jun. 7, 2016, Amgen Inc.
U.S. Appl. No. 15/175,821, filed Jun. 7, 2016, Amgen Inc.
U.S. Appl. No. 15/175,824, filed Jun. 7, 2016, Amgen Inc.

(Continued)

*Primary Examiner* — Rebecca Anderson
(74) *Attorney, Agent, or Firm* — Markus Bergauer

(57) ABSTRACT

The present invention provides MDM2 inhibitor compounds of Formula (I), or the pharmaceutically acceptable salts thereof, wherein the variables are defined above, which compounds are useful as therapeutic agents, particularly for the treatment of cancers. The present invention also relates to pharmaceutical compositions that contain an MDM2 inhibitor of Formula (I).

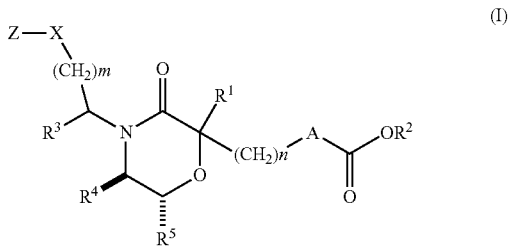

37 Claims, No Drawings

(56) References Cited

U.S. PATENT DOCUMENTS

| | | | |
|---|---|---|---|
| 2016/0002185 | A1 | 1/2016 | Bartberger et al. |
| 2016/0137667 | A1 | 5/2016 | Bartberger et al. |
| 2016/0264526 | A1 | 9/2016 | Bio et al. |
| 2016/0287570 | A1 | 10/2016 | Bio et al. |
| 2016/0289178 | A1 | 10/2016 | Caille et al. |
| 2016/0289190 | A1 | 10/2016 | Bio et al. |
| 2016/0289243 | A1 | 10/2016 | Bio et al. |
| 2017/0144971 | A1 | 5/2017 | Bartberger et al. |

FOREIGN PATENT DOCUMENTS

| | | | |
|---|---|---|---|
| EP | 0408357 | A2 | 1/1991 |
| TW | 200801000 | A | 1/2008 |
| TW | 200808781 | A | 2/2008 |
| WO | WO95/23135 | A1 | 8/1995 |
| WO | WO96/06095 | A1 | 2/1996 |
| WO | WO97/30045 | A1 | 8/1997 |
| WO | WO99/06397 | A2 | 2/1999 |
| WO | WO99/31507 | A1 | 6/1999 |
| WO | WO02/17912 | A1 | 3/2002 |
| WO | WO02/089738 | A2 | 11/2002 |
| WO | WO02/094787 | A1 | 11/2002 |
| WO | WO03/051359 | A1 | 6/2003 |
| WO | WO2004/031149 | A1 | 4/2004 |
| WO | WO2005/110996 | A1 | 11/2005 |
| WO | WO2005/123691 | A1 | 12/2005 |
| WO | WO2006/097261 | A1 | 9/2006 |
| WO | WO2006/107859 | A2 | 10/2006 |
| WO | WO2006/107860 | A2 | 10/2006 |
| WO | WO2007/063013 | A1 | 6/2007 |
| WO | WO2007/104664 | A1 | 9/2007 |
| WO | WO2008/005268 | A1 | 1/2008 |
| WO | WO2008/010953 | A2 | 1/2008 |
| WO | WO2008/021338 | A2 | 2/2008 |
| WO | WO2008/021339 | A2 | 6/2008 |
| WO | WO2008/076754 | A2 | 6/2008 |
| WO | WO2008/110793 | A1 | 9/2008 |
| WO | WO2008/125487 | A1 | 10/2008 |
| WO | WO2008/141975 | A1 | 11/2008 |
| WO | WO2009/004430 | A1 | 1/2009 |
| WO | WO2009/007750 | A1 | 1/2009 |
| WO | WO2009/047161 | A1 | 4/2009 |
| WO | WO2009/082038 | A2 | 7/2009 |
| WO | WO2009/114950 | A1 | 9/2009 |
| WO | WO2009/156735 | A2 | 12/2009 |
| WO | WO2010/028862 | A1 | 3/2010 |
| WO | WO2010/031713 | A1 | 3/2010 |
| WO | WO2010/121995 | A1 | 10/2010 |
| WO | WO2011/023677 | A1 | 3/2011 |
| WO | WO2011/067185 | A1 | 6/2011 |
| WO | WO2011/076786 | A1 | 6/2011 |
| WO | WO2011/153509 | A1 | 12/2011 |
| WO | WO2013/049250 | A1 | 4/2013 |
| WO | WO2014/130470 | A1 | 8/2014 |
| WO | WO2014/134201 | A1 | 9/2014 |
| WO | WO2014/151863 | A1 | 9/2014 |
| WO | WO2014/200937 | A1 | 12/2014 |
| WO | WO2015/070224 | A2 | 5/2015 |

OTHER PUBLICATIONS

Alexakis, A. et al., "Monoaminals of Glyoxal: Versatile Chirons," J. Am. Chem. Soc. 117, 10767-10768 (1995).

Okaku, N. et al., "Synthesis of Chelating Agents. IV.*1 Synthesis and Chelating Behavior of 1-Phenyl-ethylenedinitrilo-N, N, N', N'-tetraacetic Acid and 1, 2-Diphenyl-ethylenedinitrilo-N, N, N', N'-tetraacetic Acid*2," Bulletin of the Chemical Society of Japan 40, 2326-2332 (1967).

U.S. Appl. No. 15/412,804, filed Jan. 23, 2017, Amgen Inc.

Allen, P., "Aliphatic Sulfinic Acids. I. Analysis and Identification," J. Org. Chem. 7, 23-30 (1942).

Braverman, M. et al., "Product Class 3: Alkanesulfinic Acids and Acyclic Derivatives," Science of Synthesis 39, 187-243 (2007).

Fenton et al., "CCCVI.—Influence of Poles and Polar Linkings on the Course pursued by Elimination Reactions. Part IV. Further Experiments on the Olefinic Degradation of Sulphones." J. Chem. Soc., 2338-2341 (1929).

Notice of Allowance dated Jan. 20, 2017 for U.S. Appl. No. 15/175,805, filed Jun. 7, 2016, pp. 1-10.

Notice of Allowance dated Oct. 27, 2016 for U.S. Appl. No. 15/008,342, filed Jan. 27, 2016, pp. 1-7.

U.S. Appl. No. 15/008,342, filed Jan. 27, 2015, Amgen Inc.

Office Action dated Dec. 24, 2014 for U.S. Appl. No. 14/347,628, filed Mar. 26, 2014, pp. 1-21.

Office Action dated May 13, 2015 for U.S. Appl. No. 14/347,628, filed Mar. 26, 2014, pp. 1-7.

Office Action dated Aug. 10, 2015 for U.S. Appl. No. 14/347,628, filed Mar. 26, 2014, pp. 1-4.

Written Opinion of the International Searching Authority, PCT/US2011/039184, dated Sep. 9, 2011, pp. 1-5.

U.S. Appl. No. 14/768,529, filed Aug. 18, 2015, Amgen Inc.

Allen, J. G. et al., "Discovery and Optimization of Chromenotriazolopyrimidines as Potent Inhibitors of the Mouse Double Minute 2-Tumor Protein 53 Protein-Protein Interaction," Journal of Medicinal Chemistry 52(22), 7044-7053 (2009).

Anthony, N. J. et al., "Pseudo-Allylic A1,3 Strain as a Conformational Control Element: Stereoselective Syntheses of ψ[CH2O] Pseudodipeptides," Tetrahedron Letters 36(22), 3821-3824 (1995).

Garcia Ruano, J. L. et al., "Synthesis of 2-phenyl-, 3-phenyl-, cis-2,3-diphenyl-, and trans-2,3-diphenyl-1,4-thiazanes and derivatives (N-methyl, N-alkoxycarbonyl, S-oxides, and S,S-dioxides)," Journal of Organic Chemistry 57(15), 4215-4224 (1992).

Gattermann, L. "The Practical Methods of Organic Chemistry" 1896, MacMillan: New York, pp. 1-14.

Gonzalez, A. Z. et al., "Novel Inhibitors of the MDM2-p53 Interaction Featuring Hydrogen Bond Acceptors as Carboxylic Acid Isosteres," Journal of Medicinal Chemistry 57(7), 2963-2988 (2014).

Guidance for Industry ANDAs: Pharmaceutical Solid Polymorphism Chemistry Manufacturing, and Controls Information, U.S. Department of Health and Human Services, Food and Drug Administration, Center for Drug Evaluation and Research (CDER), Jul. 2007, pp. 1-13.

He, Q. et al., "Novel morpholin-3-one derivatives induced apoptosis and elevated the level of P53 and Fas in A549 lung cancer cells," Bioorganic & Medicinal Chemistry 15(11), 3889-3895 (2007).

International Search Report, PCT/US2011/039184, dated Sep. 9, 2011, pp. 1-3.

International Search Report, PCT/US2012/057389, dated Jan. 18, 2013, pp. 1-4.

International Search Report, PCT/US2014/016971, dated May 15, 2014, pp. 1-5.

International Search Report, PCT/US2014/018759, dated Jun. 12, 2014, pp. 1-5.

International Search Report, PCT/US2014/026584, dated Jun. 26, 2014, pp. 1-5.

International Search Report, PCT/US2014/041594, dated Aug. 18, 2014, pp. 1-7.

Lawrence, H. R. et al., "Identification of a disruptor of the MDM2-p53 protein-protein interaction facilitated by high-throughput in silico docking," Bioorganic & Medicinal Chemistry Letters 19, 3756-3759 (2009).

Michelsen, K. et al., "Ordering of the N-Terminus of Human MDM2 by Small Molecule Inhibitors," Journal American Chemical Society 134(41), 17059-17067 (2012).

Morissette, S. L. et. al. "High-throughput crystallization: polymorphs, salts, co-crystals and solvates of pharmaceutical solids," Advanced Drug Delivery Reviews 56, 275-300 (2004).

Nakayama, H. et al., "Hydrates of Organic Compounds. X. The Formation of Clathrate Hydrates of Tetrabutylammonium Alkanesulfonates," Bulletin of the Chemical Society of Japan, 833-837 (1986).

Notice of Allowance dated Oct. 29, 2015 for U.S. Appl. No. 14/316,586, filed Jun. 26, 2014.

Patani, G. A. et al., "Bioisosterism: A Rational Approach in Drug Design," Chemical Reviews 96(8), 3147-3176 (1996).

(56) References Cited

OTHER PUBLICATIONS

Rew, Y. et al., "Structure-Based Design of Novel Inhibitors of the MDM2-p53 Interaction," Journal of Medicinal Chemistry 55(11), 4936-4954.
Rothweiler, U. et al., "Isoquinolin-1-one Inhibitors of the MDM2-p53 Interaction," ChemMedChem 3(7), 1118-1128.
Stefanovsky, J. N. et al., "Ueber die Verhaeltnisse bei Ringschlussreaktionen epimerer 2-Amino-1,2-diphenyl-aethanole," Chem. Ber. 102, 717-727 (1969), cited on p. 19 of in Office Action dated Dec. 24, 2014 for U.S. Appl. No. 14/347,628, pp. 1-21 (attached).
Sun, D. et al., "Discovery of AMG 232, a Potent, Selective, and Orally Bioavailable MDM2-p53 Inhibitor in Clinical Development," Journal of Medicinal Chemistry 57(4), 1454-1472 (2014).
Written Opinion of the International Searching Authority, PCT/US2011/039814, dated Sep. 9, 2011, pp. 1-5.
Written Opinion of the International Searching Authority, PCT/US2012/057389, dated Jan. 18, 2013, pp. 1-6.
Written Opinion of the International Searching Authority, PCT/US2014/016971, dated May 15, 2014, pp. 1-3.
Written Opinion of the International Searching Authority, PCT/US2014/018759, dated Jun. 12, 2014, pp. 1-7.
Written Opinion of the International Searching Authority, PCT/US2014/026584, dated Jun. 26, 2014, pp. 1-6.
Written Opinion of the International Searching Authority, PCT/US2014/041594, dated Aug. 18, 2014, pp. 1-12.
Zeitler, J. A. et al. "Characterization of Temperature-Induced Phase Transitions in Five Polymorphic Forms of Sulfathiazole by Terahertz Pulsed Spectroscopy and Differential Scanning Calorimetry," Journal of Pharmaceutical Sciences 95(11), 2486-2498 (2006).
Damia, G. et al., "Contemporary pre-clinical development of anti-cancer agents—What are the optimal preclinical models?," European Journal of Cancer 45, 2768-2781 (2009).
Johnson, J. et al., "Relationships between drug activity in NCI preclinical in vitro and in vivo models and early clinical trials," British Journal of Cancer 84, 1424-1431 (2001).
Ledford, H., "US cancer institute overhauls cell lines," Nature 530, 391 (2016).
Ocana, A. et al., "Preclinical development of molecular-targeted agents for cancer," Nat. Rev. Clin. Oncol. 8, 200-209 (2011).
Office Action dated Mar. 15, 2017 for U.S. Appl. No. 15/175,798, filed Jun. 7, 2016, pp. 1-10.
Office Action dated Mar. 21, 2017 for U.S. Appl. No. 15/175,824, filed Jun. 7, 2016, pp. 1-6.
Office Action dated Mar. 22, 2017 for U.S. Appl. No. 15/175,798, filed Jun. 7, 2016, pp. 1-11.
Office Action dated Mar. 28, 2017 for U.S. Appl. No. 14/768,529, filed Aug. 18, 2015, pp. 1-23.
Office Action dated Mar. 6, 2017 for U.S. Appl. No. 15/163,186, filed May 24, 2016, pp. 1-10.
Patel, S. et al., "Small-molecule inhibitors of the p53-HDM2 interaction for the treatment of cancer," Expert Opin. Investig. Drugs 17, 1865-1882 (2008).
Sharma, S. V. et al., "Cell line-based platforms to evaluate the therapeutic efficacy of candidate anticancer agents," Nature Reviews 10, 241-253 (2010).

\* cited by examiner

HETEROARYL ACID MORPHOLINONE COMPOUNDS AS MDM2 INHIBITORS FOR THE TREATMENT OF CANCER

This application is a national stage application under 35 U.S.C. §371 of International Application No. PCT/US2014/026584, having an international filing date of Mar. 13, 2014, which claims the benefit of U.S. Provisional Patent Application No. 61/784,230, filed Mar. 14, 2013.

FIELD OF THE INVENTION

The present invention relates to compounds that are MDM2 inhibitors that are useful as therapeutic agents, particularly for the treatment of cancers. The invention also relates to pharmaceutical compositions that contain a MDM2 inhibitor.

BACKGROUND OF THE INVENTION p53 is a tumor suppressor and transcription factor that responds to cellular stress by activating the transcription of numerous genes involved in cell cycle arrest, apoptosis, senescence, and DNA repair. Unlike normal cells, which have infrequent cause for p53 activation, tumor cells are under constant cellular stress from various insults including hypoxia and pro-apoptotic oncogene activation. Thus, there is a strong selective advantage for inactivation of the p53 pathway in tumors, and it has been proposed that eliminating p53 function may be a prerequisite for tumor survival. In support of this notion, three groups of investigators have used mouse models to demonstrate that absence of p53 function is a continuous requirement for the maintenance of established tumors. When the investigators restored p53 function to tumors with inactivated p53, the tumors regressed.

p53 is inactivated by mutation and/or loss in 50% of solid tumors and 10% of liquid tumors. Other key members of the p53 pathway are also genetically or epigenetically altered in cancer. MDM2, an oncoprotein, inhibits p53 function, and it is activated by gene amplification at incidence rates that are reported to be as high as 10%. MDM2, in turn, is inhibited by another tumor suppressor, p14ARF. It has been suggested that alterations downstream of p53 may be responsible for at least partially inactivating the p53 pathway in $p53^{WT}$ tumors (p53 wildtype). In support of this concept, some $p53^{WT}$ tumors appear to exhibit reduced apoptotic capacity, although their capacity to undergo cell cycle arrest remains intact. One cancer treatment strategy involves the use of small molecules that bind MDM2 and neutralize its interaction with p53. MDM2 inhibits p53 activity by three mechanisms: 1) acting as an E3 ubiquitin ligase to promote p53 degradation; 2) binding to and blocking the p53 transcriptional activation domain; and 3) exporting p53 from the nucleus to the cytoplasm. All three of these mechanisms would be blocked by neutralizing the MDM2-p53 interaction. In particular, this therapeutic strategy could be applied to tumors that are $p53^{WT}$, and studies with small molecule MDM2 inhibitors have yielded promising reductions in tumor growth both in vitro and in vivo. Further, in patients with p53-inactivated tumors, stabilization of wildtype p53 in normal tissues by MDM2 inhibition might allow selective protection of normal tissues from mitotic poisons.

The present invention relates to compounds capable of inhibiting the interaction between p53 and MDM2 and activating p53 downstream effector genes. As such, compounds of the present invention would be useful in the treatment of cancers, bacterial infections, viral infections, ulcers and inflammation. In particular, the compounds of the present invention are useful to treat solid tumors such as: breast, colon, lung and prostate tumors; and liquid tumors such as lymphomas and leukemias. As used herein, MDM2 means a human MDM2 protein and p53 means a human p53 protein. It is noted that human MDM2 can also be referred to as HDM2 or hMDM2.

SUMMARY OF THE INVENTION

In embodiment 1, the present invention provides compounds of Formula I, or pharmaceutically acceptable salts thereof,

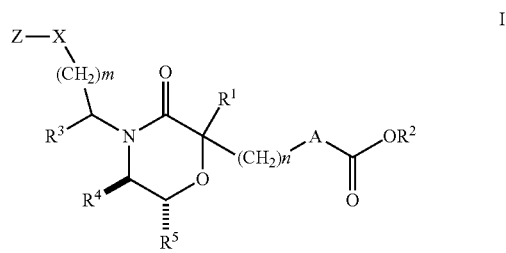

wherein:
X is $S(=O)_2$ or $-S(=O)_2N(R^a)-$;
Z is $C_{1-6}$alkyl or $C_{3-6}$cyclolalkyl;
A is a 5 or 6 membered heteroaryl group containing a nitrogen atom, or an N-oxide thereof, and from 0 to 2 additional heteroatoms independently selected from O, N, or S, where the heteroaryl group may be unsubstituted or substituted with from 1 to 3 substituents independently selected from, halo, $C_{1-6}$alkyl, $-OC_{1-6}$alkyl, $-OCF_3$, $-CF_3$, $-CHF_2$ or $-CHF$;
$R^1$ is hydrogen or $C_{1-6}$alkyl, where the alkyl group can be unsubstituted or substituted with from 1 to 3 substituents independently selected from halo, $-OH$, $-OC_{1-6}$alkyl, $-OCF_3$, $-CF_3$, $-CN$, $-CHF_2$ or $-CHF$;
$R^2$ is hydrogen or $C_{1-6}$alkyl;
$R^3$ is $C_{3-6}$cycloalkyl or $C_{1-6}$alkyl, where the cycloalkyl or alkyl group can be unsubstituted or substituted with from 1 to 2 substituents independently selected from halo, $C_{1-6}$alkyl, $-CH_2CF_3$, $-CF_3$, $-OCF_3$, $-CHF_2$ or $-CHF$;
$R^4$ is a phenyl or pyridyl group which is substituted with from one to three substituents independently selected from halo or $C_{1-6}$ alkyl;
$R^5$ is a phenyl or pyridyl group which is substituted with from one to three substituents independently selected from halo or $C_{1-6}$ alkyl;
n is 0, 1 or 2;
m is 1 or 2; and
$R^a$ is hydrogen, $C_{1-6}$alkyl, $C_{3-6}$cycloalkyl or phenyl, where the phenyl or cycloalkyl group is unsubstituted or substituted with from one to three halo groups.

In embodiment 2, the present invention provides compounds in accordance with embodiment 1, or pharmaceutically acceptable salts thereof, wherein X is $S(=O)_2$.

In embodiment 3, the present invention provides compounds in accordance with embodiment 1, or pharmaceutically acceptable salts thereof, wherein X is $-S(=O)_2N(R^a)-$.

In embodiment 4, the present invention provides compounds in accordance with any one of embodiments 1 to 3, or pharmaceutically acceptable salts thereof, wherein m is 1.

In embodiment 5, the present invention provides compounds in accordance with any one of embodiments 1 to 3, or pharmaceutically acceptable salts thereof, wherein m is 2.

In embodiment 6, the present invention provides compounds in accordance with any one of embodiments 1 to 5, or pharmaceutically acceptable salts thereof, wherein $R^1$ is hydrogen.

In embodiment 7, the present invention provides compounds in accordance with any one of embodiments 1 to 5, or pharmaceutically acceptable salts thereof, wherein $R^1$ is $C_{1-6}$alkyl.

In embodiment 8, the present invention provides compounds in accordance with any one of embodiments 1 to 5, or pharmaceutically acceptable salts thereof, wherein $R^1$ is —$CH_3$.

In embodiment 9, the present invention provides compounds in accordance with any one of embodiments 1 to 8, or pharmaceutically acceptable salts thereof, wherein $R^2$ is hydrogen.

In embodiment 10, the present invention provides compounds in accordance with any one of embodiments 1 to 8, or pharmaceutically acceptable salts thereof, wherein $R^2$ is $C_{1-6}$alkyl.

In embodiment 11, the present invention provides compounds in accordance with any one of embodiments 1 to 8, or pharmaceutically acceptable salts thereof, wherein $R^2$ is —$CH_3$ or —$CH_2CH_3$.

In embodiment 12, the present invention provides compounds in accordance with any one of embodiments 1 to 11, or pharmaceutically acceptable salts thereof, wherein $R^3$ is $C_{3-6}$ cycloalkyl or substituted $C_{3-6}$cycloalkyl.

In embodiment 13, the present invention provides compounds in accordance with any one of embodiments 1 to 11, or pharmaceutically acceptable salts thereof, wherein $R^3$ is $C_{1-6}$alkyl or substituted $C_{1-6}$alkyl.

In embodiment 14, the present invention provides compounds in accordance with any one of embodiments 1 to 11, or pharmaceutically acceptable salts thereof, wherein $R^3$ is cyclopropyl.

In embodiment 15, the present invention provides compounds in accordance with any one of embodiments 1 to 14, or pharmaceutically acceptable salts thereof, wherein $R^4$ is substituted phenyl.

In embodiment 16, the present invention provides compounds in accordance with any one of embodiments 1 to 14, or pharmaceutically acceptable salts thereof, wherein $R^4$ is halo substituted phenyl.

In embodiment 17, the present invention provides compounds in accordance with any one of embodiments 1 to 14, or pharmaceutically acceptable salts thereof, wherein $R^4$ is para-halo substituted phenyl.

In embodiment 18, the present invention provides compounds in accordance with any one of embodiments 1 to 14, or pharmaceutically acceptable salts thereof, wherein $R^4$ is para-chloro substituted phenyl.

In embodiment 19, the present invention provides compounds in accordance with any one of embodiments 1 to 18, or pharmaceutically acceptable salts thereof, wherein $R^5$ is substituted phenyl.

In embodiment 20, the present invention provides compounds in accordance with any one of embodiments 1 to 18, or pharmaceutically acceptable salts thereof, wherein $R^5$ is halo substituted phenyl.

In embodiment 21, the present invention provides compounds in accordance with any one of embodiments 1 to 18, or pharmaceutically acceptable salts thereof, wherein $R^5$ is meta-halo phenyl.

In embodiment 22, the present invention provides compounds in accordance with any one of embodiments 1 to 18, or pharmaceutically acceptable salts thereof, wherein $R^5$ is meta-chloro phenyl.

In embodiment 23, the present invention provides compounds in accordance with any one of embodiments 1 to 22, or pharmaceutically acceptable salts thereof, wherein n is 1.

In embodiment 24, the present invention provides compounds in accordance with any one of embodiments 1 to 22, or pharmaceutically acceptable salts thereof, wherein n is 0.

In embodiment 25, the present invention provides compounds in accordance with any one of embodiments 1 to 24, or pharmaceutically acceptable salts thereof, wherein A is a 5 membered heteroaryl group.

In embodiment 26, the present invention provides compounds in accordance with any one of embodiments 1 to 24, or pharmaceutically acceptable salts thereof, wherein A is a 6 membered heteroaryl group.

In embodiment 27, the present invention provides compounds in accordance with any one of embodiments 1 to 24, or pharmaceutically acceptable salts thereof, wherein A is pyridyl.

In embodiment 28, the present invention provides compounds in accordance with any one of embodiments 1 to 24, or pharmaceutically acceptable salts thereof, wherein A is pyridine-N-oxide.

In embodiment 29, the present invention provides compounds in accordance with any one of embodiments 1 to 24, or pharmaceutically acceptable salts thereof, wherein A is a thiazolyl group.

In embodiment 30, the present invention provides compounds in accordance with any one of embodiments 1 or 3 to 29, or pharmaceutically acceptable salts thereof, wherein $R^a$ is hydrogen.

In embodiment 31, the present invention provides compounds in accordance with any one of embodiments 1 or 3 to 29, or pharmaceutically acceptable salts thereof, wherein $R^a$ is $C_{1-6}$alkyl.

In embodiment 32, the present invention provides compounds in accordance with embodiment 1, or pharmaceutically acceptable salts thereof, wherein:
X is $S(=O)_2$;
A is pyridyl or thiazolyl;
$R^1$ is $C_{1-6}$alkyl or hydrogen;
$R^2$ is hydrogen or $C_{1-6}$alkyl;
$R^3$ is $C_{3-6}$cycloalkyl or $C_{1-6}$alkyl;
$R^4$ is a phenyl or pyridyl group which is substituted with from one to three substituents independently selected from halo;
$R^5$ is a phenyl or pyridyl group which is substituted with from one to three substituents independently selected from halo; and
m is 1.

In embodiment 33, the present invention provides compounds in accordance with embodiment 1, or pharmaceutically acceptable salts thereof, wherein:
X is $S(=O)_2$;
A is

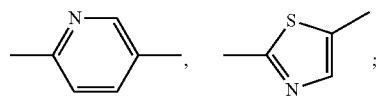

$R^1$ is —$CH_3$ or hydrogen;
$R^2$ is hydrogen;

R³ is cyclopropyl;
R⁴ is 4-chlorophenyl;
R⁵ is 3-chlorophenyl; and
m is 1.

In embodiment 34, the present invention provides compounds, or pharmaceutically acceptable salts thereof, selected from:

6-(((2S,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)methyl)nicotinic acid;

6-(((2R,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)methyl)nicotinic acid;

2-(((2R,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)methyl)-5-carboxypyridine 1-oxide;

2-(((2S,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)methyl)-5-carboxypyridine 1-oxide;

2-(((2R,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)thiazole-5-carboxylic acid;

2-(((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)thiazole-5-carboxylic acid;

6-(((2R,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)nicotinic acid;

or 6-(((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)nicotinic acid.

In embodiment 35, the present invention provides pharmaceutical compositions comprising a compound of any one of embodiments 1 to 34, or pharmaceutically acceptable salts thereof, and a pharmaceutically acceptable excipient.

In embodiment 36, the present invention provides methods of treating cancer in a subject in need thereof, the methods comprising administering to the subject an effective dosage amount of a compound according to any one of embodiments 1 to 34, or pharmaceutically acceptable salts thereof.

In embodiment 37, the present invention provides methods of embodiment 36, wherein the cancer is selected from bladder, breast, colon, rectum, kidney, liver, small cell lung cancer, non-small-cell lung cancer, esophagus, gall-bladder, ovary, pancreas, stomach, cervix, thyroid, prostate, skin, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma, Burkett's lymphoma, acute and chronic myelogenous leukemia, melanoma, endometrial cancer, head and neck cancer, glioblastoma, or osteosarcoma.

In embodiment 38, the present invention provides methods of embodiment 36, wherein the cancer is bladder cancer.

In embodiment 39, the present invention provides methods of embodiment 36, wherein the cancer is breast cancer.

In embodiment 40, the present invention provides methods of embodiment 36, wherein the cancer is colon cancer.

In embodiment 41, the present invention provides methods of embodiment 36, wherein the cancer is rectum cancer.

In embodiment 42, the present invention provides methods of embodiment 36, wherein the cancer is kidney cancer.

In embodiment 43, the present invention provides methods of embodiment 36, wherein the cancer is liver cancer.

In embodiment 44, the present invention provides methods of embodiment 36, wherein the cancer is small cell lung cancer.

In embodiment 45, the present invention provides methods of embodiment 36, wherein the cancer is non-small-cell lung cancer.

In embodiment 46, the present invention provides methods of embodiment 36, wherein the cancer is esophagus cancer.

In embodiment 47, the present invention provides methods of embodiment 36, wherein the cancer is gall-bladder cancer.

In embodiment 48, the present invention provides methods of embodiment 36, wherein the cancer is ovary cancer.

In embodiment 49, the present invention provides methods of embodiment 36, wherein the cancer is pancreas cancer.

In embodiment 50, the present invention provides methods of embodiment 36, wherein the cancer is stomach cancer.

In embodiment 51, the present invention provides methods of embodiment 36, wherein the cancer is cervix cancer.

In embodiment 52, the present invention provides methods of embodiment 36, wherein the cancer is thyroid cancer.

In embodiment 53, the present invention provides methods of embodiment 36, wherein the cancer is prostate cancer.

In embodiment 54, the present invention provides methods of embodiment 36, wherein the cancer is skin cancer.

In embodiment 55, the present invention provides methods of embodiment 36, wherein the cancer is acute lymphocytic leukemia.

In embodiment 56, the present invention provides methods of embodiment 36, wherein the cancer is chronic myelogenous leukemia.

In embodiment 57, the present invention provides methods of embodiment 36, wherein the cancer is acute lymphoblastic leukemia.

In embodiment 58, the present invention provides methods of embodiment 36, wherein the cancer is B-cell lymphoma.

In embodiment 59, the present invention provides methods of embodiment 36, wherein the cancer is T-cell-lymphoma.

In embodiment 60, the present invention provides methods of embodiment 36, wherein the cancer is Hodgkin's lymphoma.

In embodiment 61, the present invention provides methods of embodiment 36, wherein the cancer is non-Hodgkin's lymphoma.

In embodiment 62, the present invention provides methods of embodiment 36, wherein the cancer is hairy cell lymphoma.

In embodiment 63, the present invention provides methods of embodiment 36, wherein the cancer is Burkett's lymphoma.

In embodiment 64, the present invention provides methods of embodiment 36, wherein the cancer is acute myelogenous leukemia.

In embodiment 65, the present invention provides methods of embodiment 36, wherein the cancer is chronic myelogenous leukemia.

In embodiment 66, the present invention provides methods of embodiment 36, wherein the cancer is endometrial cancer.

In embodiment 67, the present invention provides methods of embodiment 36, wherein the cancer is head and neck cancer.

In embodiment 68, the present invention provides methods of embodiment 36, wherein the cancer is glioblastoma.

In embodiment 69, the present invention provides methods of embodiment 36, wherein the cancer is osteosarcoma.

In embodiment 70, the present invention provides methods of any one of embodiments 36 to 70, wherein the cancer is identified as p53 wildtype.

In embodiment 71, the present invention provides compounds in accordance with any one of embodiments 1 to 33, or pharmaceutically acceptable salts thereof, wherein Z is $C_{1-6}$alkyl.

In embodiment 72, the present invention provides compounds in accordance with any one of embodiments 1 to 33, or pharmaceutically acceptable salts thereof, wherein Z is $C_{3-6}$cycloalkyl.

DETAILED DESCRIPTION OF THE INVENTION

The present invention provides compounds of Formula I, as defined above, or pharmaceutically acceptable salts thereof. The present invention also provides pharmaceutical compositions comprising a compound of Formula I, or pharmaceutically acceptable salts thereof, and methods of treating diseases and/or conditions, such as diabetes, using compounds of Formula I, or pharmaceutically acceptable salts thereof.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$alkyl.

The term "alkoxy" means an alkyl group bonded to an oxygen atom. Representative examples of alkoxy groups include methoxy, ethoxy, tert-butoxy, propoxy and isobutoxy. Common alkoxy groups are $C_{1-8}$alkoxy.

The term "halogen" or "halo" means chlorine, fluorine, bromine or iodine.

The term "alkenyl" means a branched or straight chain hydrocarbon having one or more carbon-carbon double bonds. Representative examples alkenyl groups include ethenyl, propenyl, allyl, butenyl and 4-methylbutenyl. Common alkenyl groups are $C_{2-8}$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are $C_{2-8}$ alkynyl.

The term "cycloalkyl" means a cyclic, nonaromatic hydrocarbon. Examples of cycloalkyl groups include cyclopropyl, cyclobutyl, cyclopentyl, cyclohexyl and cycloheptyl. A cycloalkyl group can contain one or more double bond. Examples of cycloalkyl groups that contain double bonds include cyclopentenyl, cyclohexenyl, cyclohexadienyl and cyclobutadienyl. Common cycloalkyl groups are $C_{3-8}$ cycloalkyl groups. A cycloalkyl group can also be a bicyclic group comprising a cycloalkyl ring fused to an aryl or heteroaryl ring. An example of such a fused bicyclic group is tetrahydronapthalene.

The term "perfluoroalkyl" means an alkyl group in which all of the hydrogen atoms have been replaced with fluorine atoms. Common perfluoroalkyl groups are $C_{1-8}$perfluoroalkyl. An example of a common perfluoroalkyl group is —$CF_3$.

The term "acyl" means a group derived from an organic acid by removal of the hydroxy group (—OH). For example, the acyl group $CH_3C(=O)$— is formed by the removal of the hydroxy group from $CH_3C(=O)OH$.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heteroatoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 2 heteroatoms are particularly common. A heterocycloalkyl group can also be a bicyclic group comprising a heterocycloalkyl ring fused to an aryl or heteroaryl ring. Examples of such fused bicyclic ring include tetrahydroquinoline or tetrahydroisoquinoline.

It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b) pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substituents include: halogen, $C_{1-8}$alkyl, hydroxyl, $C_{1-8}$alkoxy, —$NR^xR^x$, nitro, cyano, halo or perhalo$C_{1-8}$alkyl, $C_{2-8}$alkenyl, $C_{2-8}$alkynyl, —$SR^x$, —$S(=O)_2R^x$, —$C(=O)OR^x$, —$C(=O)R^x$, wherein each $R^x$ is independently hydrogen or $C_1$-$C_8$ alkyl. It is noted that when the substituent is —$NR^xR^x$, the $R^x$ groups may be joined together with the nitrogen atom to form a ring.

The term "oxo", when used as a substituent, means the =O group, which is typically attached to a carbon atom.

A group or atom that replaces a hydrogen atom is also called a substituent.

Any particular molecule or group can have one or more substituent depending on the number of hydrogen atoms that can be replaced.

The symbol "—" represents a covalent bond and can also be used in a radical group to indicate the point of attachment to another group. In chemical structures, the symbol is commonly used to represent a methyl group in a molecule.

The term "comprising" is meant to be open ended, including the indicated component but not excluding other elements.

The symbol "—" represents a covalent bond and can also be used in a radical group to indicate the point of attachment to another group. In chemical structures, the symbol is commonly used to represent a methyl group in a molecule.

The term "therapeutically effective amount" means an amount of a compound that ameliorates, attenuates or eliminates one or more symptom of a particular disease or condition, or prevents or delays the onset of one or more symptom of a particular disease or condition.

The terms "patient" and "subject" may be used interchangeably and mean animals, such as dogs, cats, cows, horses, sheep and humans. Particular patients are mammals. The term patient includes males and females.

The term "pharmaceutically acceptable" means that the referenced substance, such as a compound of Formula I, or a salt of a compound of Formula I, or a formulation containing a compound of Formula I, or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

The term "cancer" means a physiological condition in mammals that is characterized by unregulated cell growth. General classes of cancers include carcinomas, lymphomas, sarcomas, and blastomas.

The compounds of the present invention can be used to treat cancer. The methods of treating a cancer comprise administering to a patient in need thereof a therapeutically effective amount of a compound of Formula I, or a pharmaceutically acceptable salt thereof.

The compounds of the present invention can be used to treat tumors. The methods of treating a tumor comprise administering to a patient in need thereof a therapeutically effective amount of a compound of Formula I, or a pharmaceutically acceptable salt thereof.

The invention also concerns the use of a compound of the present invention in the manufacture of a medicament for the treatment of a condition such as a cancer.

Cancers which may be treated with compounds of the present invention include, without limitation, carcinomas such as cancer of the bladder, breast, colon, rectum, kidney, liver, lung (small cell lung cancer, and non-small-cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). Other cancers that can be treated with a compound of the present invention include endometrial cancer, head and neck cancer, glioblastoma, malignant ascites, and hematopoietic cancers.

Particular cancers that can be treated by the compounds of the present invention include soft tissue sarcomas, bone cancers such as osteosarcoma, breast tumors, bladder cancer, Li-Fraumeni syndrome, brain tumors, rhabdomyosarcoma, adrenocortical carcinoma, colorectal cancer, non-small cell lung cancer, and acute myeleogenous leukemia (AML).

In a particular embodiment of the invention that relates to the treatment of cancers, the cancer is identified as p53wildtype (p53$^{WT}$). In another particular embodiment, the cancer is identified as p53$^{WT}$ and CDKN2A mutant. In another aspect, the present invention provides a diagnostic for determining which patients should be administered a compound of the present invention. For example, a sample of a patient's cancer cells may be taken and analyzed to determine the status of the cancer cells with respect to p53 and/or CDKN2A. In one aspect, a patient having a cancer that is p53$^{WT}$ will be selected for treatment over patients having a cancer that is mutated with respect to p53. In another aspect, a patient having a cancer that is both p53$^{WT}$ and has a mutant CDNK2A protein is selected over a patient that does not have these characteristics. The taking of a cancer cells for analyses is well known to those skilled in the art. The term "p53$^{WT}$" means a protein encoded by genomic DNA sequence no. NC_000017 version 9 (7512445 . . . 7531642)(GenBank); a protein encoded by cDNA sequence no. NM_000546 (GenBank); or a protein having the GenBank sequence no. NP_000537.3. The term "CDNK2A mutant" means a CDNK2A protein that in not wildtype. The term "CDKN2A wildtype" means a protein encoded by genomic DNA sequence no. 9:21957751-21984490 (Ensemble ID); a protein encoded by cDNA sequence no. NM_000077 (GenBank) or NM_058195 9GenBank) or; or a protein having the GenBank sequence no. NP_000068 or NP_478102.

The compounds of the present invention can also be used to treat hyperproliferative disorders such as thyroid hyperplasia (especially Grave's disease), and cysts (such as hypervascularity of ovarian stroma, characteristic of polycystic ovarian syndrome (Stein-Leventhal syndrome)).

The compounds of the present invention can also be used to treat the following diseases or conditions: asthma, chronic obstructive pulmonary disease (COPD), emphysema, psoriasis, contact dermatitis, conjunctivitis, allergic rhinitis, systemic lupus erythematosus (SLE), ulcerative colitis, Crohn's disease, multiple sclerosis, rheumatoid arthritis, inflammatory bowel disease, Alzheimer's disease, atherosclerosis and Huntington's disease.

The compounds of the present invention can also be used to treat inflammatory diseases, hypoxia, ulcers, viral infections, bacterial infections, and bacterial sepsis.

The compounds of Formula I, or the pharmaceutically acceptable salts thereof, may also be administered in combination with one or more additional pharmaceutically active compounds/agents. In a particular embodiment, the additional pharmaceutically active agent is an agent that can be used to treat a cancer. For example, an additional pharmaceutically active agent can be selected from antineoplastic agents, anti-angiogenic agents, chemotherapeutic agents and peptidal cancer therapy agents. In yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof. It is noted that the additional pharmaceutically active compounds/agents may be a traditional small organic chemical molecules or can be macromolecules such as a proteins, antibodies, peptibodies, DNA, RNA or fragments of such macromolecules.

Examples of specific pharmaceutically active agents that can be used in the treatment of cancers and that can be used in combination with one or more compound of the present invention include: methotrexate; tamoxifen; fluorouracil; 5-fluorouracil; hydroxyurea; mercaptopurine; cisplatin; carboplatin; daunorubicin; doxorubicin; etoposide; vinblastine; vincristine; pacitaxel; thioguanine; idarubicin; dactinomycin; imatinib; gemcitabine; altretamine; asparaginase; bleomycin; capecitabine; carmustine; cladisat. aq. NaCl solution; cyclophosphamine; cytarabine; decarazine; docetaxel; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant and nelarabine, or a pharmaceutically acceptable salt thereof.

Additional pharmaceutically active agents that can be used in the treatment of cancers and that can be used in combination with one or more compound of the present invention include: vascular endothelial growth factor (VEGF) inhibitors, hepatocyte growth factor/scatter factor (HGF/SF) inhibitors, angiopoietin 1 and/or 2 inhibitors, tumor necrosis factor-related apoptosis-inducing ligand (TRAIL) agonists, recombinant human apo2 ligand (TRAIL), insulin-like growth factor 1 receptor (IGFR-1) inhibitors, cFMS inhibitors, HER 2 inhibitors, c-met inhibitors, aurora kinase inhibitors, CDK 4 and/or 6 inhibitors, and B-raf inhibitors.

Further additional pharmaceutically active agents that can be used in the treatment of cancers and that can be used in combination with one or more compound of the present invention include antibody drug conjugates (ADCs) whereby an antibody that binds to a protein, preferably on a cancer cell, is conjugated using a linker with a chemical compound that is detrimental to the cancer cell. Examples of chemical compounds that are detrimental to a cancer cell include maytansinoids derivatives and auristatin derivatives.

Still further additional pharmaceutically active agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 319; AMG 386; AMG 479 (Ganitumab); AMG 511, AMG 900, AMG 655 (Conatumumab); AMG 745; AMG 951; and AMG 706 (Motesanib), or a pharmaceutically acceptable salt thereof.

In another aspect, the present invention relates to the use of the compounds of the present invention in combination with one or more pharmaceutical agent that is an inhibitor of a protein in the phosphatidylinositol 3-kinase (PI3K) pathway. Combinations of compounds of the present invention along with inhibitors of proteins in the PI3K pathway have shown synergy in cancer cell growth assays, including enhanced apoptosis and cell killing. Examples of proteins in the PI3K pathway include PI3K, mTOR and PKB (also known as Akt). The PI3K protein exists in several isoforms including α, β, δ, or γ. It is contemplated that a PI3K inhibitor that can be used in combination with a compound of the present invention can be selective for one or more isoform. By selective it is meant that the compounds inhibit one or more isoform more that other isoforms. Selectivity is a concept well known to those is the art and can be measured with well known activity in vitro or cell-based assays. Preferred selectivity includes greater than 2 fold, preferably 10 fold, or more preferably 100 fold greater selectivity for one or more isoform over the other isoforms. In one aspect, the PI3K inhibitors that can be used in combination with compounds of the present invention is a PI3K α selective inhibitor. In another aspect the compound is a PI3K δ selective inhibitor.

Examples of PI3K inhibitors that can be used in combination with one or more compounds of the present invention include those disclosed in the following: PCT published application no. WO2010/151791; PCT published application no. WO2010/151737;
PCT published application no. WO2010/151735; PCT published application no. WO2010151740; PCT published application no. WO2008/118455; PCT published application no. WO2008/118454; PCT published application no. WO2008/118468; U.S. published application no. US20100331293; U.S. published application no. US20100331306; U.S. published application no. US20090023761; U.S. published application no. US20090030002; U.S. published application no. US20090137581; U.S. published application no. US2009/0054405; U.S. published application no. U.S. 2009/0163489; U.S. published application no. US 2010/0273764; U.S. published application no. U.S. 2011/0092504; or PCT published application no. WO2010/108074.

Preferred PI3K inhibitors for use in combination with compounds of the present invention include:

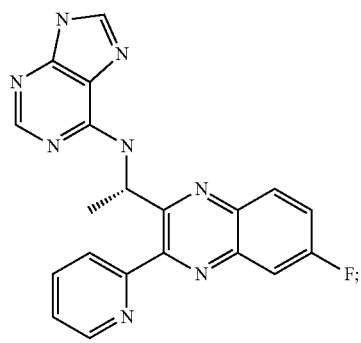

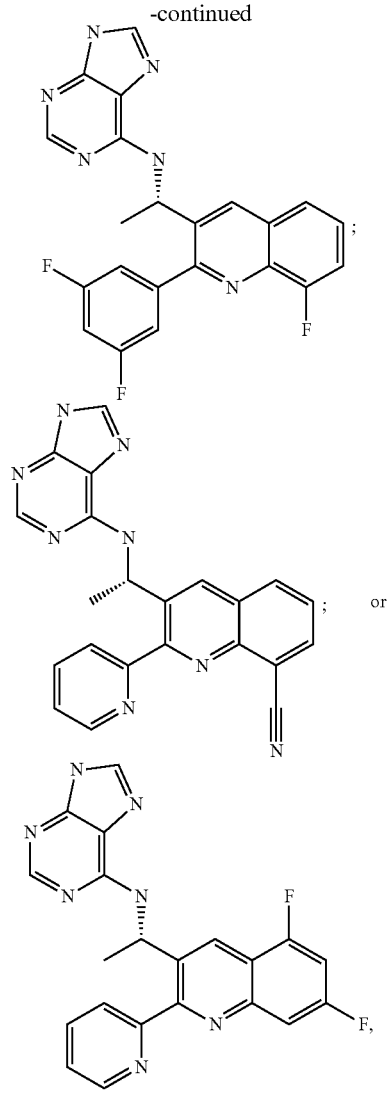

or a pharmaceutically acceptable salt thereof.

Also preferred is a compound of Formula IIa below, or a pharmaceutically acceptable salt thereof,

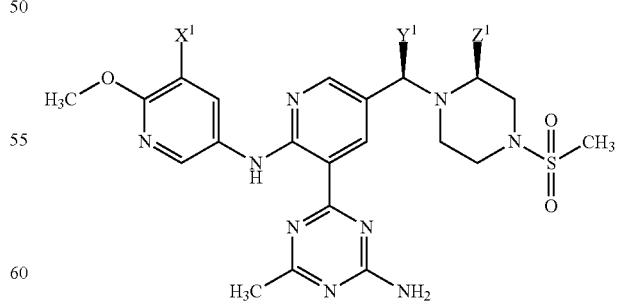

wherein $X^1$ is fluorine or hydrogen; $Y^1$ is hydrogen or methyl; and $Z^1$ is hydrogen or methyl.

Compounds that inhibit both PI3K and mTOR (dual inhibitors) are known. In still another aspect, the present invention provides the use of dual PI3K and mTOR inhibitors for use in combination with a compound of the present invention.

mTOR is a protein in the PI3K pathway. It is another aspect of the present invention to use an mTOR inhibitor in combination with one or more compounds of the present invention. mTOR inhibitors that can be used in combination with compounds of the present invention include those disclosed in the following documents: PCT published application no. WO2010/132598 or PCT published application no. WO2010/096314.

PKB (Akt) is also a protein in the PI3K pathway. It is another aspect of the present invention to use an mTOR inhibitor in combination with one or more compounds of the present invention. PKB inhibitors that can be used in combination with compounds of the present invention include those disclosed in the following documents: U.S. Pat. No. 7,354,944; U.S. Pat. No. 7,700,636; U.S. Pat. No. 7,919,514; U.S. Pat. No. 7,514,566; U.S. patent application publication no. US 2009/0270445 A1; U.S. Pat. No. 7,919,504; U.S. Pat. No. 7,897,619; or PCT published application no. WO 2010/083246 A1.

The compounds of the present invention can be used in combination with CDK4 and/or 6 inhibitors. CDK 4 and/or 6 inhibitors that can be used in combination with compounds of the present invention include those disclosed in the following documents: PCT published application no. WO 2009/085185 or U.S. patent application publication no. US2011/0097305.

The compounds of the present invention can also be used in combination with pharmaceutically active agents that treat nausea. Examples of agents that can be used to treat nausea include: dronabinol; granisetron; metoclopramide; ondansetron; and prochlorperazine; or a pharmaceutically acceptable salt thereof.

In addition, the compounds of the present invention can be used in combination with other agents that can be used to treat cancer such as acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflornithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracil/oteracil/tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon alfa-N1; interferon alfa-n3; interferon alfacon-1; interferon alpha natural; interferon beta; interferon beta-1a; interferon beta-1b; interferon gamma natural; interferon gamma-1a; interferon gamma-1b; interleukin-1 beta; iobenguane; irsogladine; lanreotide; LC 9018 (Yakult); leflunomide; lenograstim; lentinan sulfate; letrozole; leukocyte alpha interferon; leuprorelin; levamisole+fluorouracil; liarozole; lobaplatin; lonidamine; lovastatin; masoprocol; melarsoprol; metoclopramide; mifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; pentosan polysulfate sodium; pentostatin; picibanil; pirarubicin; rabbit antithymocyte polyclonal antibody; polyethylene glycol interferon alfa-2a; porfimer sodium; raltitrexed; rasburicase; rhenium Re 186 etidronate; RH retinamide; romurtide; samarium (153 Sm) lexidronam; sargramostim; sizofiran; sobuzoxane; sonermin; strontium-89 chloride; suramin; tasonermin; tazarotene; tegafur; temoporfin; teniposide; tetrachlorodecaoxide; thymalfasin; thyrotropin alfa; toremifene; tositumomab-iodine 131; treosulfan; tretinoin; trilostane; trimetrexate; triptorelin; tumor necrosis factor alpha natural; ubenimex; bladder cancer vaccine; Maruyama vaccine; melanoma lysate vaccine; valrubicin; verteporfin; virulizin; zinostatin stimalamer; abarelix; AE 941 (Aeterna); ambamustine; antisense oligonucleotide; bcl-2 (Genta); APC 8015 (Dendreon); dexaminoglutethimide; diaziquone; EL 532 (Elan); EM 800 (Endorecherche); eniluracil; etanidazole; fenretinide; filgrastim SDO1 (Amgen); galocitabine; gastrin 17 immunogen; HLA-B7 gene therapy (Vical); granulocyte macrophage colony stimulating factor; histamine dihydrochloride; ibritumomab tiuxetan; ilomastat; IM 862 (Cytran); interleukin-2; iproxifene; LDI 200 (Milkhaus); leridistim; lintuzumab; CA 125 monoclonal antibody(MAb) (Biomira); cancer MAb (Japan Pharmaceutical Development); HER-2 and Fc MAb (Medarex); idiotypic 105AD7 MAb (CRC Technology); idiotypic CEA MAb (Trilex); LYM-1-iodine 131 MAb (Techniclone); polymorphic epithelial mucin-yttrium 90 MAb (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (Pfizer); TA 077 (Tanabe); tetrathiomolybdate; thaliblastine; thrombopoietin; tin ethyl etiopurpurin; tirapazamine; cancer vaccine (Biomira); melanoma vaccine (New York University); melanoma vaccine (Sloan Kettering Institute); melanoma oncolysate vaccine (New York Medical College); viral melanoma cell lysates vaccine (Royal Newcastle Hospital); or valspodar. It is noted that the agents recited above may also be administered as pharmaceutically acceptable salts when appropriate.

The compounds of the present invention may also be used in combination with radiation therapy, hormone therapy, surgery and immunotherapy, which therapies are well known to those skilled in the art.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Ophthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$Cl_2$) alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-a-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention. Also, for example, all keto-enol or imine-enamine forms of the compounds are included in this invention.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{18}O$, $^{31}P$, $^{32}P$, $^{35}S$, $^{18}F$, and $^{36}Cl$. In one aspect, the present invention relates to compounds wherein one or more hydrogen atom is replaced with deuterium ($^{2}H$) atoms.

Compounds of the present invention that contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents, published patent applications and other publications recited herein are hereby incorporated by reference.

The examples presented below illustrate specific embodiments of the present invention. These examples are meant to be representative and are not intended to limit the scope of the claims in any manner. Unless otherwise noted, when a percent is used herein with respect to a solid, the percent is by weight with respect to the referenced solid composition. When a percent is used herein with respect to a liquid, the percent is by volume with respect to the referenced solution.

$^{1}$H-NMR spectra were acquired with a 500 MHz Bruker Avance III spectrometer system (Bruker Biospin, Billerica, Mass.) equipped with a Bruker 5-mm z-axis gradient BBI probe; or with a 400 MHz Bruker Avance II or Avance III spectrometer system equipped with a Bruker 5-mm z-axis gradient BBO probe. Samples were typically dissolved in 600 μL of either DMSO-$d_6$ or $CD_3OD$ for NMR analysis. $^{1}$H chemical shifts are referenced relative to the residual proton signals from the deuterated solvents used for the analysis at d 2.50 ppm for DMSO-$d_6$ and d 3.30 ppm for $CD_3OD$.

Significant peaks are tabulated and typically include: number of protons, multiplicity (s, singlet; d, doublet; dd, doublet of doublets; t, triplet; q, quartet; m, multiplet; br s, broad singlet) and coupling constant(s) in Hertz.

Electron Ionization (EI) mass spectra were typically recorded on an Agilent Technologies 6140 Quadrupole LC/MS mass spectrometer. Mass spectrometry results are reported as the ratio of mass over charge, sometimes followed by the relative abundance of each ion (in parentheses). Starting materials in the Examples below are typically either available from commercial sources such as Sigma-Aldrich, St. Louis, Mo., or via literature procedures.

The following abbreviations may be used herein:

~ about
+ve or pos. ion positive ion
Δ heat
Ac acetyl
$Ac_2O$ acetic anhydride
aq aqueous
AcOH acetic acid
Bn benzyl
Boc tert-butyloxycarbonyl
BSA bovine serum albumin
Bu butyl
Bz benzoyl
Calcd or Calc'd calculated
Conc. concentrated
CSA camphor-10-sulfonic acid
d day(s)
DBU 1,8-diazabicyclo[5.4.0]undec-7-ene
DCE dichloroethane
DCM dichloromethane
DDQ 2,3-dichloro-5,6-dicyano-1,4-benzoquinone
DEA diethylamine
Dess-Martin periodinane; 1,1,1-triacetoxy-1,1-dihydro-1,2-benziodoxol-3-(1H)-one Dess-Martin reagent
DIEA or DIPEA diisopropylethylamine
DMAP 4-dimethylaminopyridine
DME 1,2-dimethoxyethane
DMF N,N-dimethylformamide
DMSO dimethyl sulfoxide
DPPA diphenylphosphoryl azide
dr diastereomeric ratio
DTT dithiothreitol
DVB divinylbenzene
EDC N-ethyl-N'-(3-dimethylaminopropyl)carbodiimide
ee or e.e. enantiomeric excess
eq equivalent
ESI or ES electrospray ionization
Et ethyl
$Et_2O$ diethyl ether Et₃N triethylamine
EtOAc ethyl acetate
EtOH ethyl alcohol
g gram(s)
h hour(s)
HATU O-(7-azabenzotriazol-1-yl)-N,N,N',N'-tetramethyl-uronium hexafluorophosphate
HBTU O-benzotriazole-N,N,N',N'-tetramethyl-uronium-hexafluorophosphate
Hex hexanes
HMPA hexamethylphosphoramide
HOAt 1-hydroxy-7-azabenzotriazole
HOBt hydroxybenzotriazole
HPLC high pressure liquid chromatography
IPA or iPrOH isopropyl alcohol
Jones reagent solution of chromium(IV)oxide and sulfuric acid in water
KHMDS potassium hexamethyldisilazide
KOAc potassium acetate
LCMS, LC-MS or LC/MS liquid chromatography mass spectrometry
LDA lithium diisopropylamide
LHMDS or LiHMDS lithium hexamethyldisilazide
L-Selectride® lithium tri-sec-butylborohydride (Sigma-Aldrich, St. Louis)
M molar (mol L⁻¹)
mCPBA m-chloroperoxybenzoic acid
Me methyl
MeCN acetonitrile
MeI iodomethane
MeOH methyl alcohol
mg milligram(s)
min minute(s)
mL milliliter(s)
M mole(s)
MS mass spectrometry
MsCl methanesulfonyl chloride
MTBE or MtBE methyl tert-butyl ether
m/z mass-to-charge ratio
NaHMDS sodium hexamethyldisilazide
NaOtBu sodium tert-butoxide
NBS N-bromosuccinimide
nBuLi n-butyl lithium
NMO N-methylmorpholine-N-oxide
NMP 1-methyl-2-pyrrolidinone
NMR nuclear magnetic resonance
N-Selectride® sodium tri-sec-butylborohydride (Sigma-Aldrich, St. Louis)
PBS phosphate buffered saline
PMB paramethoxybenzyl
Pr propyl
ppm parts per million
PTFE polytetrafluoroethylene
p-tol para-toluoyl
rac racemic
RP-HPLC or RPHPLC reversed phase high pressure liquid chromatography
RT or rt or r.t. room temperature
sat. or sat'd or satd saturated
SFC supercritical fluid chromatography
TBAF tetrabutylammonium fluoride
TBDMS tert-butyldimethylsilyl
TBDMS-Cl tert-butyldimethylsilyl chloride
TBDPS tert-butyldiphenylsilyl
TEMPO (2,2,6,6-tetramethylpiperidin-1-yl)oxidanyl
tert or t tertiary
TFA triflouroacetic acid
THF tetrahydrofuran
TIPS triisopropylsilyl
TLC thin layer chromatography
TMS trimethylsilyl or trimethylsilane
TPAP tetrapropylammonium perruthenate
$t_R$ retention time
tBuOH tert-butyl alcohol
v/v volume per volume

EXAMPLES

General Synthetic Schemes

Compounds of the present invention generally can be prepared beginning with commercially available starting materials and using synthetic techniques known to those of skill in the art. Outlined below are some reaction schemes suitable for preparing compounds of the present invention. Further exemplification is found in the specific examples provided.

General Scheme for the Preparation of Biaryl Amino Alcohols.

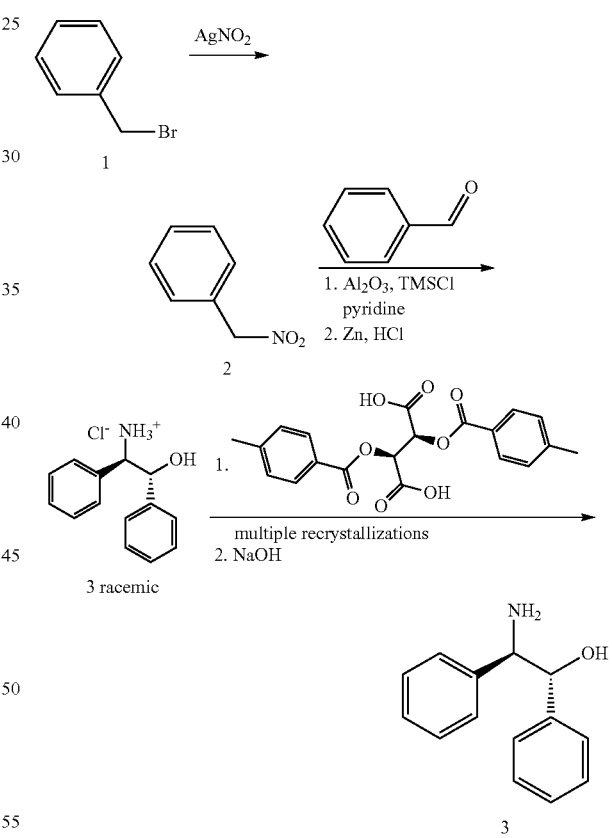

The preparation of biaryl amino alcohols such as 3 can be generally accomplished via a Henry reaction between a nitromethyl arene (such as 2) and an appropriate benzaldehyde in the presence of alumina, pyridine and trimethylsilyl chloride. Crystallization with tartrate derivatives such as (+)-di-p-toluoyl-D-tartaric acid can provide optically enriched intermediates, which can further purified through multiple recrystallizations. The nitromethyl arenes can be prepared from the corresponding arylmethyl bromides via displacement with silver nitrite.

General Scheme for the Preparation Bis Aryl Morpholinones
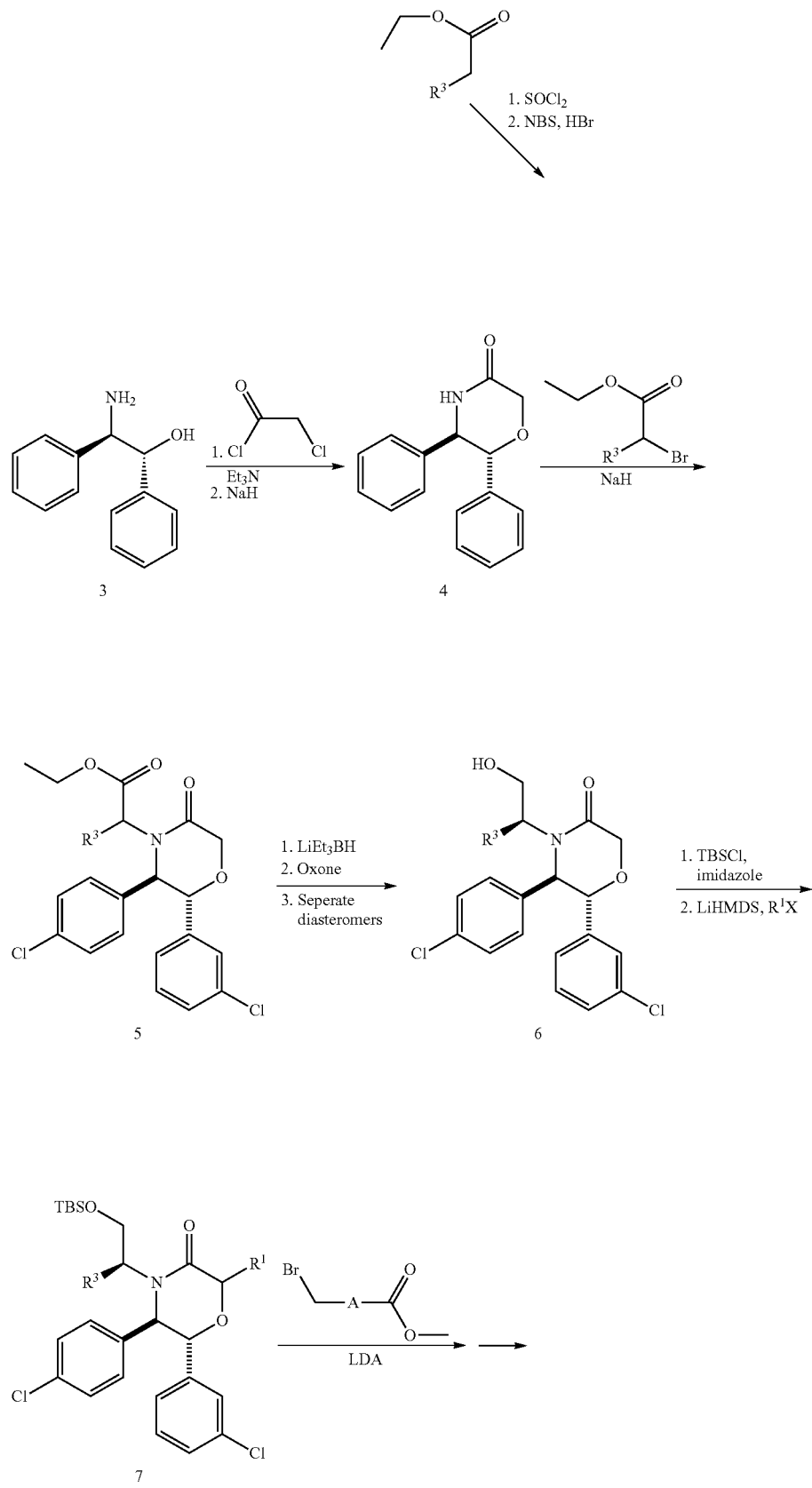

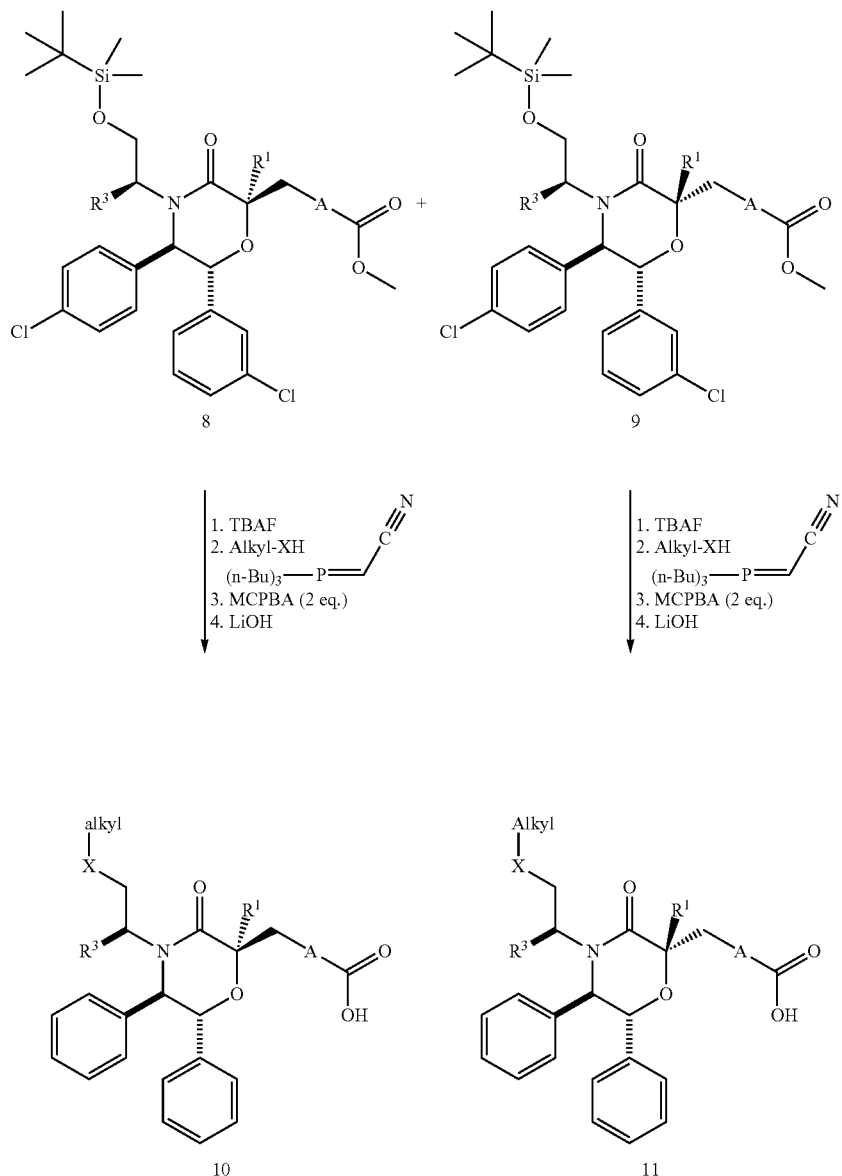

Bis aryl morpholinones such as 4 can be prepared from the reaction of amino alcohols, 3, and chloro acetyl chloride in a two-step procedure consisting of amide formation followed by intramolecular displacement of the alkyl chloride. N-Alkylation of lactams such as 4, can be accomplished by deprotonation of the lactam NH by sodium hydride, followed by addition of an appropriate α-halo ester. α-Halo esters can be prepared by halogenations (typically bromination) of the corresponding ester. Esters such as those contained in compound 5 can be reduced selectively in the presence of the morpholinone by hydride to provide the corresponding primary alcohol, such as the one shown as compound 6. These diastereomeric alcohols can often be separated by column chromatography at this stage of the synthesis. The primary alcohol can be protected with a tert-butyldimethylsilyl group and the product can be C-alkylated at the 2-position of the lactam ring using bases such as LiHMDS and an appropriate electrophile ($R^1X$). In many cases the heteroaryl substituent can be added in one step via alkylation of the lactam ring in the presence of a base such as LDA and the appropriate electrophile containing the heteroaryl substituent to give diastereomeric compounds such as 8 and 9, which can be separated by column chromatography. Deprotection of the silyl group, followed by a Mitsunobu reaction can be used to install the desired alkyl-X group as shown in the generic scheme above. When X is a sulfur, it can be oxidized to a sulfone with 3-chloroperbenzoic acid. Other groups can be alkylated directly. Finally, ester hydrolysis produces the desired carboxylic acids such as 10 and 11.

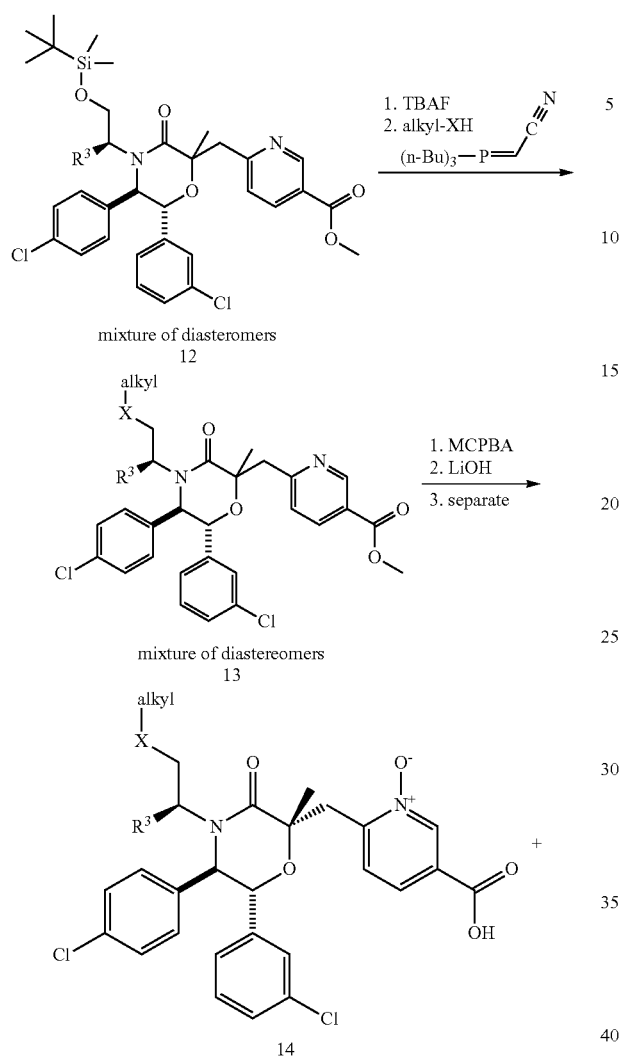

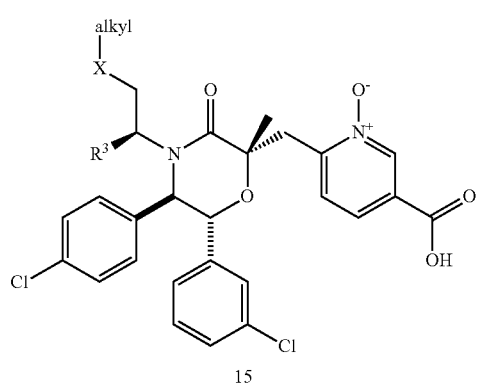

When A is a pyridine, it can be further oxidized to the N-oxide by addition of 3-chloroperbenzoic acid. When X is a sulfide, both the sulfur and the pyridine can be oxidized by the addition of the appropriate number of equivalents of 3-chloroperbenzoic acid. In the example procedure, diasteromeric lactams such as 12 can be deprotected and undergo a Mitsunobu reaction to install an appropriate X-group. Oxidation of the pyridine to the N-oxide and deprotection of the methyl ester provide compounds such as 14 and 15, which can be separated.

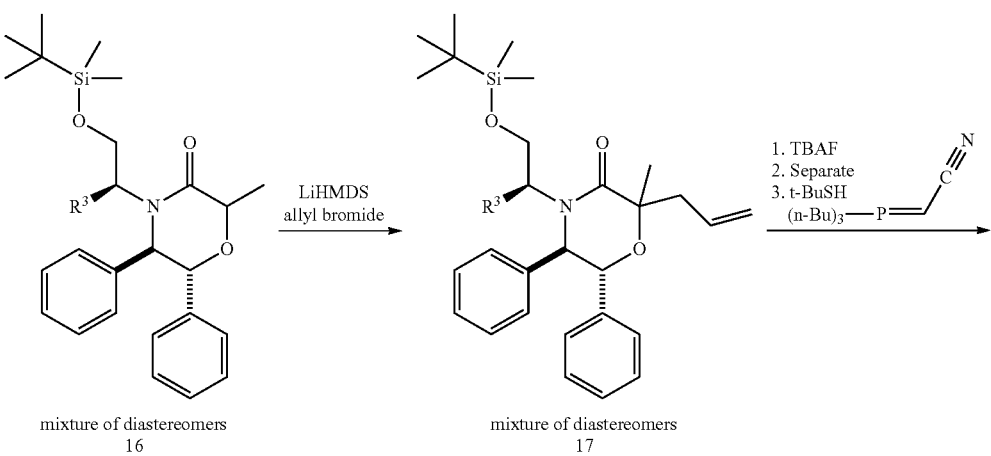

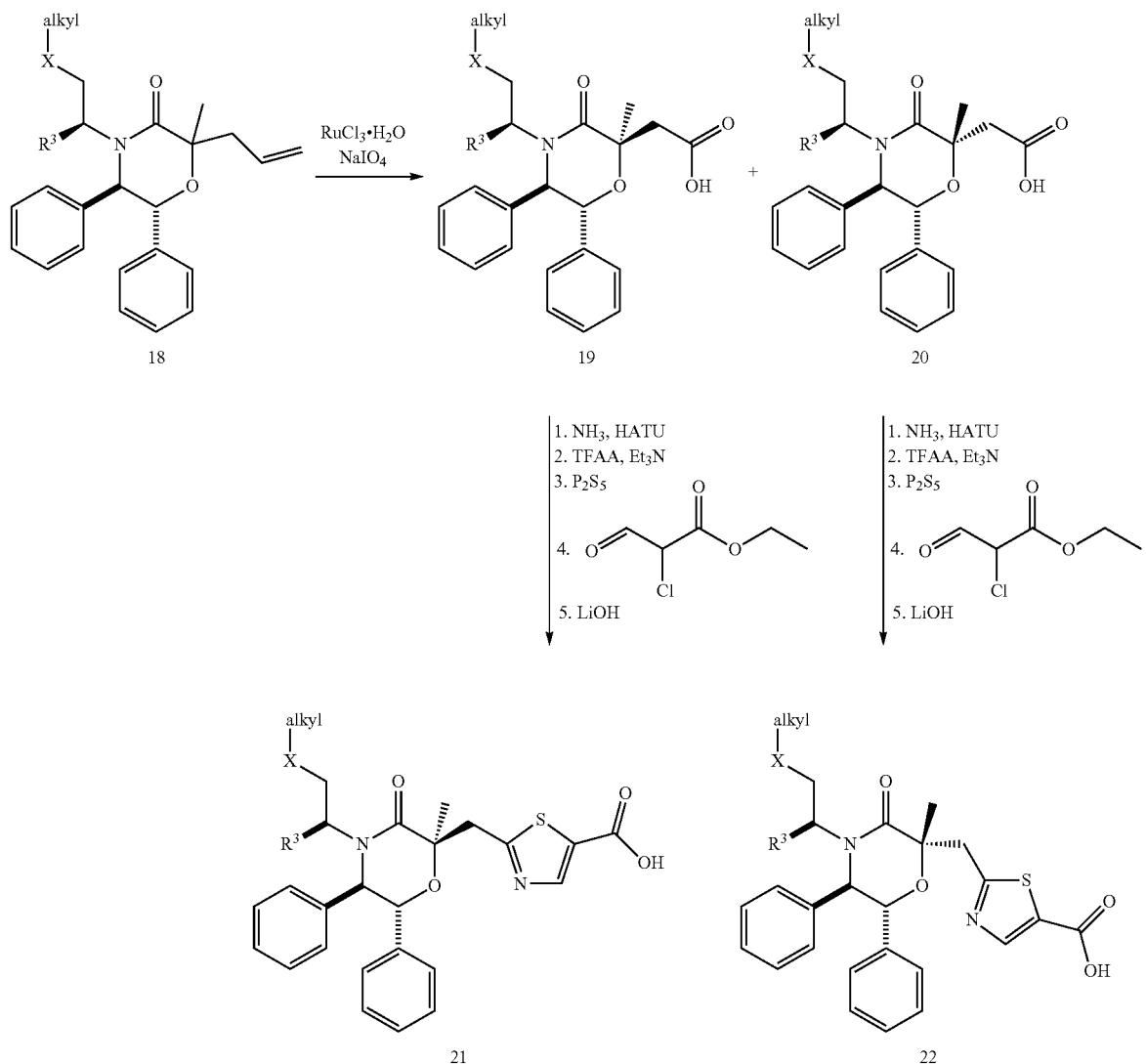

Sometimes it is difficult to directly alkylate the morpholinone ring with a particular heteroaryl fragment. Fortunately, there are numerous methods for preparing the heterocyclic rings from readily accessible functional groups. As a representative example, the preparation of diasteromeric thiazoles is shown above.

Allylation at the C-2 positions of morpholinones such as 16 can be accomplished with allyl bromide in the presence of LiHMDS to provide structures such as 17. Deprotection, separation of diastereomers, and a Mitsunobu reaction with an appropriate alkyl-XH provides intermediate 18. The allyl group of compound 18 provides a convenient handle for the installation of many heterocycles. In the case of thiazole, the allyl group can be oxidized with ruthenium(III) chloride and sodium periodate to provide the corresponding carboxylic acids 19 and 20. Conversion of the acid to the primary amide and dehydration forms the nitrile, another useful intermediate for heterocycle formation. The thioamide can be prepared by addition of diphosphorous pentasulfide which is readily converted to the thiazole by addition of ethyl 2-chloro-3-oxopropanoate. The methyl ester is readily hydrolyzed with lithium hydroxide to form the desired carboxylic acids 21 and 22.

Intermediate A (1R,2R)-2-Amino-1-(3-chlorophenyl)-2-(4-chlorophenyl)ethanol

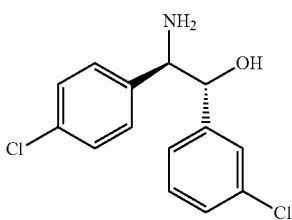 [SMILES: N[C@H](c1ccc(Cl)cc1)[C@H](O)c1cccc(Cl)c1]

Step A. 1-Chloro-4-(nitromethyl)benzene

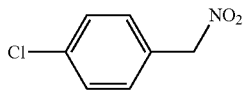 [SMILES: O=[N+]([O-])Cc1ccc(Cl)cc1]

A suspension of silver nitrite (392 g) in diethyl ether (1.6 L) was cooled to 0° C. and a solution of 4-chlorobenzyl bromide (395 g, 1.92 mol) in diethyl ether (1.6 L) was added dropwise over 1 hour (the temperature was maintained below 3° C. during addition). The reaction mixture was stirred for 16 hours at 0° C. in the dark. Then the mixture was filtered and the solids were washed with diethyl ether (3×50 mL). The combined filtrates were concentrated under reduced pressure. The residue was purified by column chromatography on silica gel (gradient elution of 0% to 10% ethyl acetate in heptane) to give the title compound.

Step B. (1R,2R)-2-Amino-1-(3-chlorophenyl)-2-(4-chlorophenyl)ethanol hydrochloride and (1S,2S)-2-Amino-1-(3-chlorophenyl)-2-(4-chlorophenyl)ethanol hydrochloride

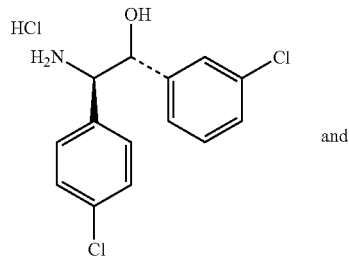

and

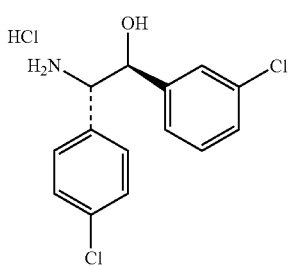

1-Chloro-4-(nitromethyl)-benzene (205 g, 1.19 mol, Intermediate A, Step A), alumina (135 g), pyridine (96 mL, 1.19 mol) and chlorotriethylsilane (200 mL, 180 g, 1.19 mol) were added to a flask containing 3-chlorobenzaldehyde (135 mL, 168 g, 1.19 mol). The flask was covered in aluminum foil and spun for 16 hours in the dark at room temperature on a rotary evaporator. The resulting thick paste was filtered and washed with isopropanol. The filtrate was divided into two equal portions and used in the next step.

The two portions were processed separately in the following manner: hydrochloric acid (1 M, 7 L, 7 mol) was added, and then zinc powder (800 g, 12.3 mol) was added in several portions. The reaction mixture was stirred until the observed exothermic reaction (to 35° C.) was complete (approximately 90 minutes). Next, the mixture was cooled to 0° C. and basified with 30% sodium hydroxide to a pH of about 10. The suspension was filtered through a pad of Celite® (J. T. Baker, Phillipsberg, N.J., diatomaceous earth) and the filter cake was washed with dichloromethane. The filtrate was transferred to a reparatory funnel, and the layers were separated. The aqueous layer was extracted with dichloromethane. The combined organic layers were dried over sodium sulfate, filtered, and the filtrate was concentrated under reduced pressure. The residue was dissolved in tert-butyl methyl ether (1.5 L) and cooled to 0° C. Then 4 N hydrochloric acid in dioxane (375 mL, 1.5 mol) was added dropwise. The solid was collected by filtration. The solid was purified by crystallization from dioxane/ethanol to give the title compounds as a racemic mixture.

Step C. (1R,2R)-2-Amino-1-(3-chlorophenyl)-2-(4-chlorophenyl)ethanol

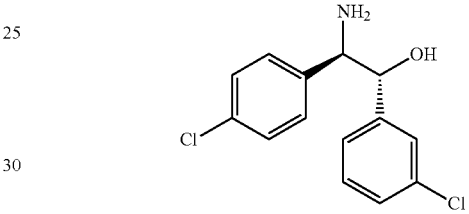

A racemic mixture of (1R,2R)-2-amino-1-(3-chlorophenyl)-2-(4-chlorophenyl)ethanol and (1S,2S)-2-amino-1-(3-chlorophenyl)-2-(4-chlorophenyl)ethanol (57 g, 0.2 mol; Intermediate A, Step B) was dissolved in ethanol (2.65 L) and (+)-di-p-toluoyl-D-tartaric acid (68.4 g, 0.169 mol) was added. The mixture was heated to reflux and water was added until the solution became clear (175 mL). The mixture was seeded with seeding crystals (enantiomeric excess of 95%) and allowed to cool to room temperature over a period of 16 hours. The mixture was filtered and the solid was washed with ethanol and dried to give the salt, which was determined to have an enantiomeric excess of 75%. This salt was recrystallized twice from 12.5:1 ethanol/water (36 mL/gram of salt) using seed crystals to initialize crystallization to provide the salt with 97.6% enantiomeric excess. The salt was dissolved in 1:1 ethyl acetate/2 N aqueous sodium hydroxide. The layers were separated and the aqueous layer was extracted with ethyl acetate. The combined organic layers were washed with brine, dried over sodium sulfate, filtered and the filtrate was concentrated under reduced pressure to give the title compound with 97.8% enantiomeric excess. Enantiomeric excess was determined by HPLC (Chiralpak® AD-H column, Chiral Technologies, Inc., West Chester, Pa., eluting with 5% isopropanol/hexanes).

(1R,2R)-2-amino-1-(3-chlorophenyl)-2-(4-chlorophenyl) ethanol: $t_R$=20.1 minutes; $[\alpha]_D^{23.5}$=+92.7° (c=0.385, in methanol).

(1S,2S)-2-amino-1-(3-chlorophenyl)-2-(4-chlorophenyl) ethanol: $t_R$=21.7 minutes.

Example 1

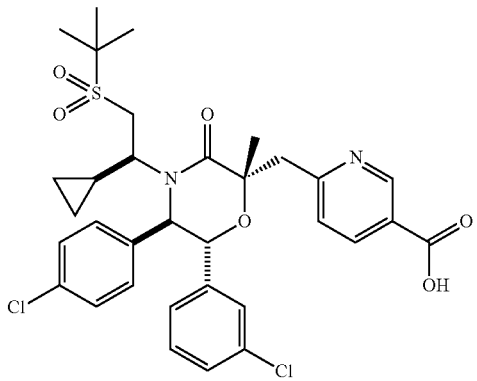

6-(((2S,5R,6R)-4-((S)-2-(tert-Butylsulfonyl)-1-cyclopropylethyl)-6-(3-chlorophenyl)-5-(4-chlorophenyl)-2-methyl-3-oxomorpholin-2-yl)methyl)nicotinic acid

Step A. (5R,6R)-6-(3-Chlorophenyl)-5-(4-chlorophenyl)morpholin-3-one

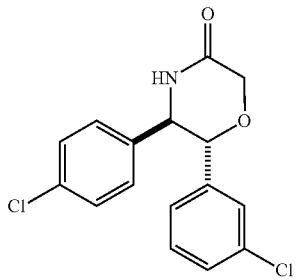

Chloroacetyl chloride (0.16 mL, 2.0 mmol) was added to a solution of (1R,2R)-2-amino-1-(3-chlorophenyl)-2-(4-chlorophenyl)ethanol (Intermediate A, 0.47 g, 1.67 mmol) and triethylamine (0.35 mL, 2.5 mmol) in tetrahydrofuran at 0° C. After stirring at 0° C. for 1 hour, saturated aqueous ammonium chloride solution (10 mL) and ethyl acetate (20 mL) were added. The layers were separated and the combined organic layer was washed with water (3×10 mL) dried over magnesium sulfate, filtered, and the filtrate was concentrated under a vacuum to give 2-chloro-N-((1R,2R)-2-(3-chlorophenyl)-1-(4-chlorophenyl)-2-hydroxyethyl)acetamide as a light yellow oil which was taken to the next step without further purification. MS (ESI) m/z: 380.0 [M+Na]$^+$.

2-Chloro-N-((1R,2R)-2-(3-chlorophenyl)-1-(4-chlorophenyl)-2-hydroxyethyl)acetamide was dissolved in tetrahydrofuran (15 mL) and treated with several portions of sodium hydride (60% dispersion in mineral oil, 0.167 g, 4.16 mmol) over a period of 5 minutes. After stirring at room temperature for 5 hours, saturated aqueous ammonium chloride solution (10 mL) and ethyl acetate (20 mL) were added. The layers were separated and the combined organic layers were washed with water (3×10 mL), dried over magnesium sulfate, filtered, and the filtrate was concentrated under a vacuum to give the resulting material as a yellow oil. This was absorbed onto a plug of silica gel and purified by flash chromatography on silica gel (gradient elution of 0% to 30% acetone in hexanes, to provide the title compound as yellow oil.

$^1$H NMR (400 MHz, CDCl$_3$, δ, ppm): 7.47-7.54 (m, 1H), 7.46-7.54 (m, 1H), 7.34-7.42 (m, 2H), 7.29-7.32 (m, 2H), 7.26-7.29 (m, 1H), 7.13-7.25 (m, 1H), 6.98 (d, J=8.41 Hz, 1H), 4.57-4.65 (m, 1H), 4.45 (d, J=9.98 Hz, 1H), 4.00 (d, J=5.67 Hz, 2H). MS (ESI) m/z: 322.2 [M+H]$^+$.

Racemic ethyl 2-bromo-2-cyclopropylacetate

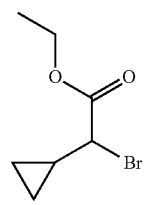

The above compound was prepared by adding a solution of 2-cyclopropylacetic acid (24.7 g, 247 mmol) in anhydrous dichloromethane (250 mL) to thionyl chloride (22 mL, 302 mmol) dropwise over 5 minutes at 25° C. After refluxing for 2 hours, the reaction was cooled to room temperature, and N-bromosuccinimide (53.6 g, 301 mmol) and hydrogen bromide (48% aqueous solution; 0.195 mL, 1.727 mmol) were added successively at 25° C. The mixture was refluxed for 3 days, and then cooled to room temperature.

Absolute ethanol (200 mL) was added and the resulting dark brown solution was stirred at room temperature for one hour. The reaction mixture was concentrated under reduced pressure, and the residue was suspended in carbon tetrachloride (300 mL) and filtered through a glass filter. The filtrate was concentrated under the reduced pressure. The resulting product was purified by flash chromatography (silica gel, two 330 g columns, eluent: 5% ethyl acetate in hexanes) to provide racemic ethyl 2-bromo-2-cyclopropylacetate.

$^1$H NMR (400 MHz, CDCl$_3$, δ, ppm): 4.24 (m, 2H), 3.58 (d, J=12.0 Hz, 1H), 1.58 (m, 1H), 0.90-0.80 (m, 2H), 0.53 (m, 1H), 0.42 (m, 1H), 1.3 (t, J=8.0 Hz, 3H).

Step B. (S)-Ethyl 2-((2R,3R)-2-(3-chlorophenyl)-3-(4-chlorophenyl)-5-oxomorpholino)-2-cyclopropylacetate and (R)-ethyl 2-((2R,3R)-2-(3-chlorophenyl)-3-(4-chlorophenyl)-5-oxomorpholino)-2-cyclopropylacetate

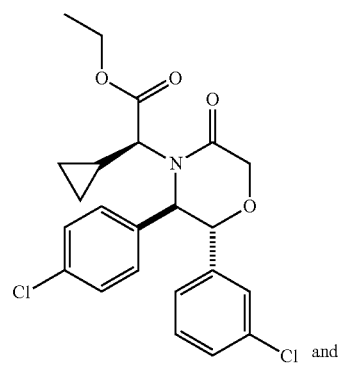

and

37

-continued

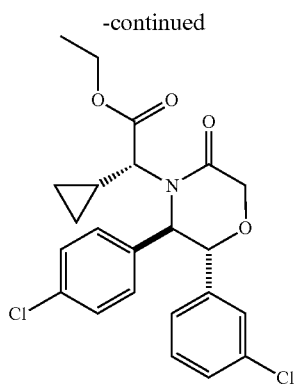

Sodium hydride (60% dispersion in mineral oil, 1.07 g, 26.7 mmol) was added to a solution of (5R,6R)-6-(3-chlorophenyl)-5-(4-chlorophenyl)morpholin-3-one (4.3 g, 13.4 mmol, Example 1, Step A) in dimethylformamide (26.7 mL) at 0° C., and the mixture was stirred at this temperature for 30 minutes. Racemic ethyl 2-bromo-2-cyclopropylacetate (preparation described above, 3.71 mL, 26.7 mmol) in dimethylformamide (40 mL) was added dropwise and the mixture was stirred at room temperature for 2 hours. The reaction was quenched with saturated ammonium chloride (10 mL) and diluted with diethyl ether (10 mL). The solution was washed with 10% citric acid (10 mL), 5% NaHCO₃ (10 mL), water (10 mL), and brine (10 mL), and then dried with magnesium sulfate. The solvent was evaporated under reduced pressure, and the residue was purified by flash chromatography on silica gel (120 g, gradient elution of 20% to 50% acetone in hexanes) to provide the title compounds as a 1.2:1 mixture of diastereomers. MS (ESI) m/z: 448.0 [M+H]⁺ for both isomers.

Step C. (5R,6R)-6-(3-Chlorophenyl)-5-(4-chlorophenyl)-4-((R)-1-cyclopropyl-2-hydroxyethyl)morpholin-3-one and (5R,6R)-6-(3-chlorophenyl)-5-(4-chlorophenyl)-4-((S)-1-cyclopropyl-2-hydroxyethyl)morpholin-3-one

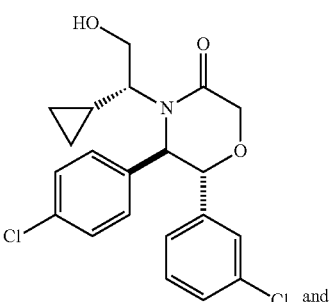

and

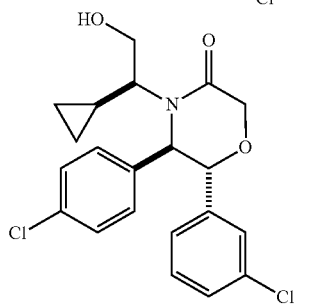

38

Lithium triethylborohydride (1.0 M solution in tetrahydrofuran, 17.4 mL, 17.4 mmol) was added to a solution of (S)-ethyl 2-((2R,3R)-2-(3-chlorophenyl)-3-(4-chlorophenyl)-5-oxomorpholino)-2-cyclopropylacetate and (R)-ethyl 2-((2R,3R)-2-(3-chlorophenyl)-3-(4-chlorophenyl)-5-oxomorpholino)-2-cyclopropylacetate (3.6 g, 8.29 mmol, Example 1, Step B) in tetrahydrofuran (8.29 mL) at 0° C. After stirring for 15 minutes, methanol was added (3 mL) dropwise over 1 minute. Then, potassium peroxymonosulfate, 15.3 g, 24.9 mmol) in water (60 mL) was added dropwise over 10 minutes. After 1 hour, saturated aqueous NaHSO₃ (9 mL) was added at room temperature. The reaction was extracted with diethyl ether (2×60 mL). The combined organic layers were dried over magnesium sulfate, filtered, and evaporated under a vacuum. The resulting material was adsorbed onto a plug of silica gel and purified by flash chromatography (330 g silica gel column, eluent: 20% acetone in hexanes) to provide (5R,6R)-6-(3-chlorophenyl)-5-(4-chlorophenyl)-4-((R)-1-cyclopropyl-2-hydroxyethyl)morpholin-3-one (fast eluting isomer) and (5R,6R)-6-(3-chlorophenyl)-5-(4-chlorophenyl)-4-((S)-1-cyclopropyl-2-hydroxyethyl)morpholin-3-one (slow eluting isomer) as off-white solids.

Characterization data for faster eluting isomer, (5R,6R)-6-(3-chlorophenyl)-5-(4-chlorophenyl)-4-((R)-1-cyclopropyl-2-hydroxyethyl)morpholin-3-one

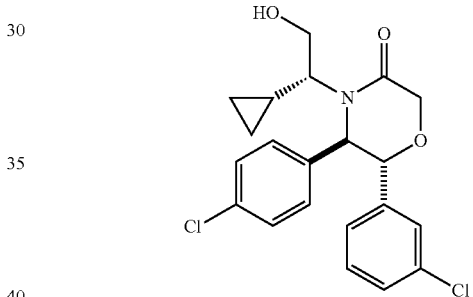

¹H NMR (400 MHz, CDCl₃, δ, ppm): 7.23 (d, J=8.41 Hz, 3H), 7.12 (d, J=17.41 Hz, 3H), 6.92 (d, J=8.41 Hz, 2H), 6.73-6.79 (m, 1H), 4.49-4.63 (m, 2H), 4.42 (s, 2H), 3.52-3.69 (m, 2H), 2.28-2.39 (m, 1H), 1.31-1.46 (m, 1H), 0.55 (s, 2H), 0.22-0.31 (m, 1H), −0.04-0.05 (m, 1H). MS (ESI) m/z: 405.4 [M+H]⁺.

Characterization data for slower eluting isomer, (5R,6R)-6-(3-chlorophenyl)-5-(4-chlorophenyl)-4-((S)-1-cyclopropyl-2-hydroxyethyl)morpholin-3-one

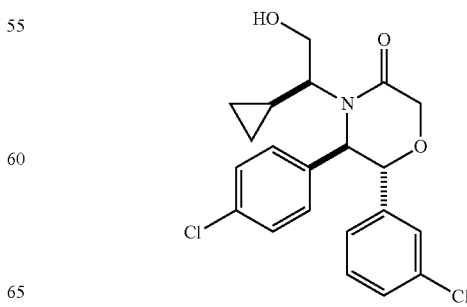

¹H NMR (400 MHz, CDCl₃, δ, ppm): 7.04-7.25 (m, 7H), 6.79 (d, J=7.63 Hz, 1H), 4.87 (d, J=7.43 Hz, 1H), 4.52 (d, J=7.43 Hz, 1H), 4.26-4.42 (m, 2H), 3.50-3.59 (m, 1H), 3.13-3.36 (m, 2H), 2.88 (br s, 1H), 0.79 (ddd, J=3.03, 4.94, 7.87 Hz, 1H), 0.40-0.57 (m, 2H), 0.11-0.23 (m, 1H), −0.10-0.06 (m, 1H). MS (ESI) m/z: 405.4 [M+H]⁺.

Step D. (5R,6R)-4-((S)-2-((tert-Butyldimethylsilyl)oxy)-1-cyclopropylethyl)-6-(3-chloro-phenyl)-5-(4-chlorophenyl)morpholin-3-one

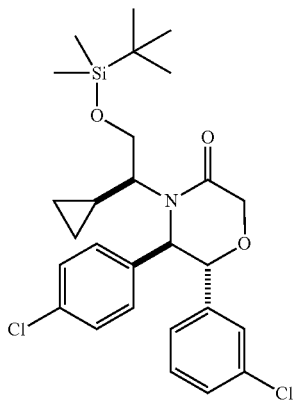

tert-Butyldimethylsilyl chloride (0.26 ml, 1.48 mmol) was added to a solution of (5R,6R)-6-(3-chlorophenyl)-5-(4-chlorophenyl)-4-((S)-1-cyclopropyl-2-hydroxyethyl)morpholin-3-one (slower eluting isomer, Example 1, Step C, 0.500 g, 1.23 mmol) and imidazole (0.16 ml, 2.46 mmol) in dichloromethane (10 mL). The mixture was stirred at room temperature for 1.5 hours.

The reaction mixture was diluted with saturated ammonium chloride (10 mL) and extracted with dichloromethane (3×30 mL). The organic extract was washed with water (30 mL) and dried over magnesium sulfate. The solution was filtered and concentrated under a vacuum to give the resulting material as a yellow oil. The material then was absorbed onto a plug of silica gel and purified by flash chromatography (24 g silica gel column, gradient elution of 10% to 30% ethyl acetate in hexanes) to provide the title compound.

¹H NMR (500 MHz, CDCl₃, δ, ppm): 7.29 (d, J=8.56 Hz, 2H), 7.22 (d, J=8.07 Hz, 1H), 7.18 (s, 1H), 7.11 (t, J=7.82 Hz, 1H), 7.06 (s, 2H), 6.76 (d, J=7.83 Hz, 1H), 4.79 (s, 1H), 4.60 (d, J=8.56 Hz, 1H), 4.42 (s, 2H), 4.27 (t, J=9.78 Hz, 1H), 3.53 (dd, J=4.65, 10.03 Hz, 1H), 2.29-2.41 (m, 1H), 1.25-1.29 (m, 1H), 0.95 (s, 9H), 0.39-0.47 (m, 1H), 0.30-0.39 (m, 1H), 0.11 (s, 3H), 0.07 (s, 3H), −0.22 to −0.05 (m, 1H), −0.65 to −0.48 (m, 1H). MS (ESI) m/z: 520.2 [M+H]⁺.

Step E. (2S,5R,6R)-4-((S)-2-((tert-Butyldimethylsilyl)oxy)-1-cyclopropylethyl)-6-(3-chloro-phenyl)-5-(4-chlorophenyl)-2-methylmorpholin-3-one and (2R,5R,6R)-4-((S)-2-((tert-butyldimethylsilyl)oxy)-1-cyclopropylethyl)-6-(3-chloro-phenyl)-5-(4-chlorophenyl)-2-methylmorpholin-3-one

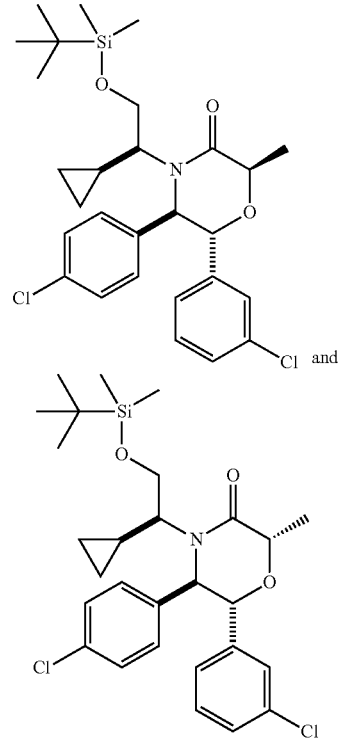

Lithium bis(trimethylsilyl)amide (1.0 M solution in tetrahydrofuran, 17.3 mL, 17.3 mmol) was added to an oven dried, 3-neck round-bottom flask containing (5R,6R)-4-((S)-2-((tert-butyldimethylsilyl)oxy)-1-cyclopropylethyl)-6-(3-chlorophenyl)-5-(4-chlorophenyl)morpholin-3-one (Example 1, Step D, 4.10 g, 7.88 mmol) in tetrahydrofuran at −78° C. under argon. Methyl iodide (1.08 mL, 17.3 mmol) in tetrahydrofuran was added. After stirring at −78° C. for 1 hour, the reaction was quenched with saturated aqueous ammonium chloride (20 mL), extracted with ethyl acetate (2×30 mL), and washed with brine (30 mL). The combined organic layer was dried (sodium sulfate) and concentrated under reduced pressure. Purification of the residue by flash column chromatography (silica gel column, gradient elution of 0% to 80% ethyl acetate in hexanes) afforded the title compounds as a white foam and a mixture of diastereomers. MS (ESI) m/z: 533.2 [M+H]⁺

Methyl 6-(bromomethyl)nicotinate

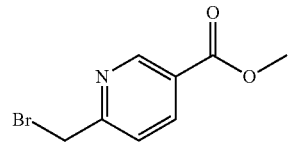

In a round-bottom flask equipped with a reflux condenser, a mixture of methyl 6-methyl nicotinate (10.0 g, 66.2 mmol), N-bromosuccinimide (7.1 g, 39.7 mmol) and benzoyl peroxide (1.6 g, 6.62 mmol) in carbon tetrachloride was stirred under nitrogen at 75° C. for 2 days. The cooled reaction mixture was filtered, the filter cake was washed with dichloromethane, and the filtrate was concentrated under a vacuum. Purification of the residue by flash column chromatography (silica gel column, gradient elution of 5% to 25% ethyl acetate in hexanes) afforded methyl 6-(bromomethyl)nicotinate as a yellow solid.

$^1$H NMR (400 MHz, CDCl$_3$, δ, ppm): 9.17 (d, J=1.56 Hz, 1H), 8.31 (dd, J=2.15, 8.02 Hz, 1H), 7.54 (d, J=8.22 Hz, 1H), 4.59 (s, 2H), 3.97 (s, 3H). MS (ESI) m/z: 230.0 [M+H]$^+$.

Step F. Methyl 6-(((2S,5R,6R)-4-((S)-2-((tert-butyldimethylsilyl)oxy)-1-cyclopropylethyl)-6-(3-chlorophenyl)-5-(4-chlorophenyl)-2-methyl-3-oxomorpholin-2-yl)methyl)nicotinate and methyl 6-(((2R,5R,6R)-4-((S)-2-((tert-butyldimethylsilyl)oxy)-1-cyclopropylethyl)-6-(3-chlorophenyl)-5-(4-chlorophenyl)-2-methyl-3-oxomorpholin-2-yl)methyl)nicotinate

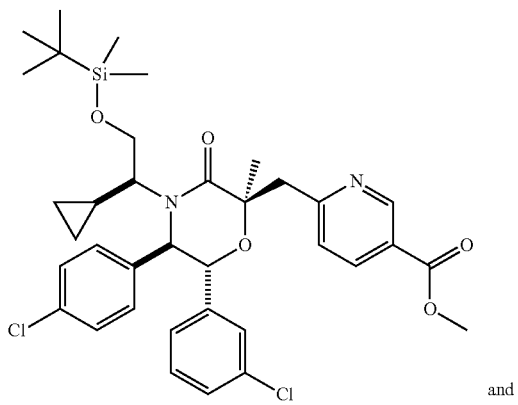

and

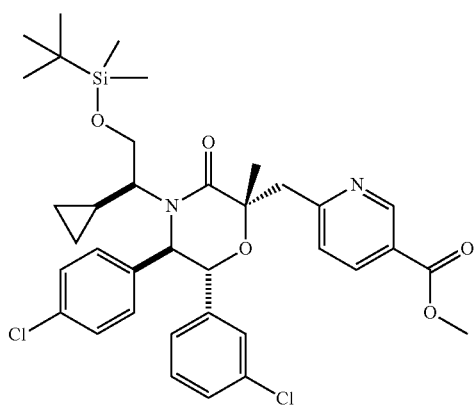

A 3-neck, oven-dried, round-bottom flask was cooled under argon and charged with diisopropylamine (2.48 mL, 17.7 mmol) and tetrahydrofuran (20 mL) and cooled to 0° C. n-Butyllithium (2.5 M in hexanes, 7.08 mL, 17.70 mmol) was added dropwise, and the reaction was stirred for 10 minutes at 0° C.

The reaction mixture was cooled to −78° C., and a solution of (2S,5R,6R)-4-((S)-2-((tert-butyldimethylsilyl)oxy)-1-cyclopropylethyl)-6-(3-chloro-phenyl)-5-(4-chlorophenyl)-2-methylmorpholin-3-one and (2R,5R,6R)-4-((S)-2-((tert-butyldimethylsilyl)oxy)-1-cyclopropylethyl)-6-(3-chloro-phenyl)-5-(4-chlorophenyl)-2-methylmorpholin-3-one (Example 1, Step E, 4.3 g, 8.04 mmol) in tetrahydrofuran (30 mL), also at −78° C., was added. After stirring at −78° C. for 15 minutes, a solution of methyl 6-(bromomethyl)nicotinate (4.07 g, 17.70 mmol) in tetrahydrofuran (20 ml) at −78° C. was added. The reaction was stirred at this temperature for 1 hour.

The resulting mixture was quenched with saturated ammonium chloride (50 mL), extracted with ethyl acetate (3×50 mL), washed with water (50 mL) and brine (50 mL). The combined organic layer was dried over magnesium sulfate, filtered and concentrated. Purification of the residue by flash column chromatography (silica gel column, gradient elution of 0% to 25% acetone in hexanes) afforded the title compounds.

Characterization data for faster eluting isomer, methyl 6-(((2S,5R,6R)-4-((S)-2-((tert-butyldimethylsilyl)oxy)-1-cyclopropylethyl)-6-(3-chlorophenyl)-5-(4-chlorophenyl)-2-methyl-3-oxomorpholin-2-yl)methyl)nicotinate

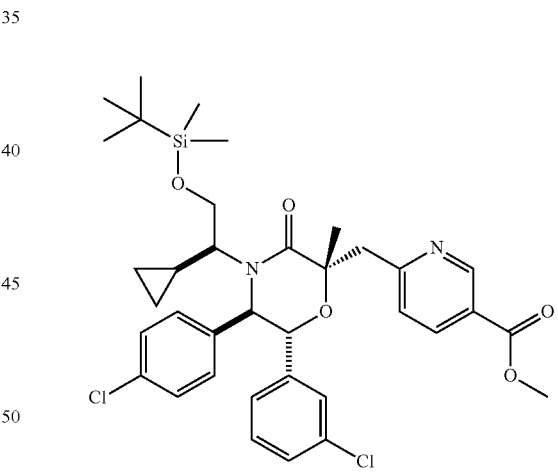

$^1$H NMR (400 MHz, CDCl$_3$, δ, ppm): 9.00 (d, J=2.15 Hz, 1H), 8.10 (d, J=7.63 Hz, 1H), 7.23 (d, J=8.22 Hz, 1H), 7.11 (d, J=8.22 Hz, 2H), 7.00-7.08 (m, 2H), 6.92 (t, J=7.83 Hz, 1H), 6.71-6.86 (m, 2H), 6.53 (d, J=7.63 Hz, 1H), 4.85 (d, J=9.78 Hz, 1H), 4.69 (d, J=9.98 Hz, 1H), 4.20 (t, J=9.98 Hz, 1H), 3.84 (s, 3H), 3.77 (d, J=13.50 Hz, 1H), 3.38-3.43 (m, J=4.50 Hz, 1H), 3.33 (d, J=14.28 Hz, 1H), 2.04-2.18 (m, 1H), 1.52 (s, 3H), 0.87 (s, 9H), 0.81 (d, J=0.78 Hz, 1H), 0.25-0.32 (m, 2H), 0.00 (s, 3H), −0.04 (s, 3H), −0.34 to −0.26 (m, J=8.80 Hz, 1H), −0.63 (dd, J=4.21, 9.29 Hz, 1H). MS (ESI) m/z: 683.2 [M+H]$^+$.

Characterization data for the slower eluting isomer, methyl 6-(((2R,5R,6R)-4-((S)-2-((tert-butyldimethylsilyl)oxy)-1-cyclopropylethyl)-6-(3-chlorophenyl)-5-(4-chlorophenyl)-2-methyl-3-oxomorpholin-2-yl)methyl)nicotinate

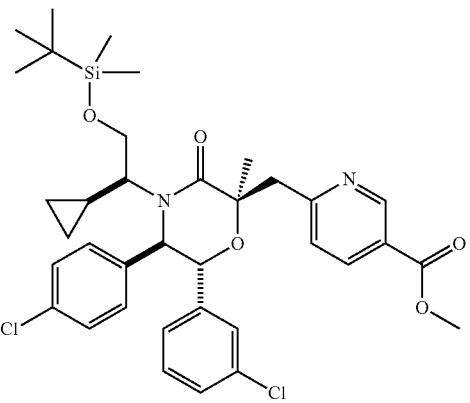

$^1$H NMR (400 MHz, CDCl$_3$, δ, ppm): 9.20-9.25 (m, 1H), 8.21-8.28 (m, 1H), 7.43 (d, J=8.02 Hz, 1H), 7.24 (br s, 2H), 7.11-7.19 (m, 2H), 7.02 (t, J=7.83 Hz, 1H), 6.92-6.98 (m, 1H), 6.86-6.91 (m, 1H), 6.52 (d, J=7.83 Hz, 1H), 4.78 (d, J=9.78 Hz, 1H), 4.62 (d, J=9.78 Hz, 1H), 3.98-4.06 (m, 1H), 3.96 (s, 3H), 3.89-3.95 (m, 1H), 3.73 (d, J=13.50 Hz, 1H), 3.46-3.52 (m, J=5.67, 10.17 Hz, 2H), 1.76 (s, 3H), 1.31-1.43 (m, 1H), 0.91 (s, 9H), 0.28-0.48 (m, 2H), 0.05 (s, 3H), 0.02 (s, 3H), −0.15 to −0.02 (m, 1H), −0.56 to −0.38 (m, 1H). MS (ESI) m/z: 683.1 [M+H]$^+$.

Step G. Methyl 6-(((2S,5R,6R)-6-(3-chlorophenyl)-5-(4-chlorophenyl)-4-((S)-1-cyclopropyl-2-hydroxyethyl)-2-methyl-3-oxomorpholin-2-yl)methyl)nicotinate

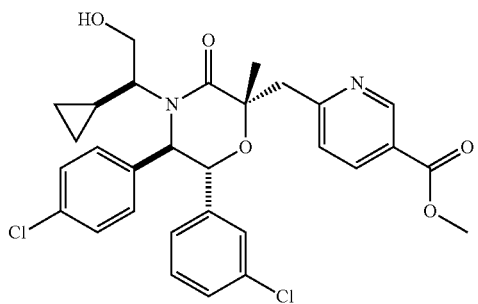

Tetrabutylammonium fluoride (1.0 M solution in tetrahydrofuran, 0.70 mL, 0.70 mmol) was added to a solution of methyl 6-(((2S,5R,6R)-4-((S)-2-((tert-butyldimethylsilyl)oxy)-1-cyclopropylethyl)-6-(3-chlorophenyl)-5-(4-chlorophenyl)-2-methyl-3-oxomorpholin-2-yl)methyl)nicotinate (Example 1, Step F, faster eluting isomer, 300 mg, 0.44 mmol) in tetrahydrofuran (5 mL) and stirred at ambient temperature overnight. The resulting mixture was quenched with saturated ammonium chloride (10 mL) washed with ethyl acetate (3×15 mL). The combined organic layer was dried over magnesium sulfate, filtered and concentrated. Purification of the residue by flash column chromatography (silica gel column, gradient elution of 0% to 25% ethyl acetate in hexanes) afforded the title compound.

$^1$H NMR (400 MHz, CDCl$_3$, δ, ppm): 9.10 (dd, J=0.78, 2.15 Hz, 1H), 8.16-8.24 (m, J=5.87 Hz, 1H), 7.29 (d, J=8.22 Hz, 1H), 7.17-7.25 (m, 3H), 7.11 (t, J=1.66 Hz, 1H), 7.07 (t, J=7.92 Hz, 1H), 6.91-7.02 (m, 2H), 6.61 (d, J=7.63 Hz, 1H), 4.85-4.92 (m, 1H), 4.73-4.82 (m, 1H), 3.95 (s, 3H), 3.82 (s, 1H), 3.56-3.66 (m, 1H), 3.34-3.48 (m, 2H), 3.12-3.25 (m, 2H), 1.60 (s, 3H), 0.68-0.78 (m, 1H), 0.48-0.68 (m, 2H), 0.21-0.31 (m, 1H), 0.04-0.19 (m, 1H). MS (ESI) m/z: 569.0 [M+H]$^+$.

Step H. Methyl 6-(((2S,5R,6R)-4-((S)-2-(tert-butylthio)-1-cyclopropylethyl)-6-(3-chlorophenyl)-5-(4-chlorophenyl)-2-methyl-3-oxomorpholin-2-yl)methyl)

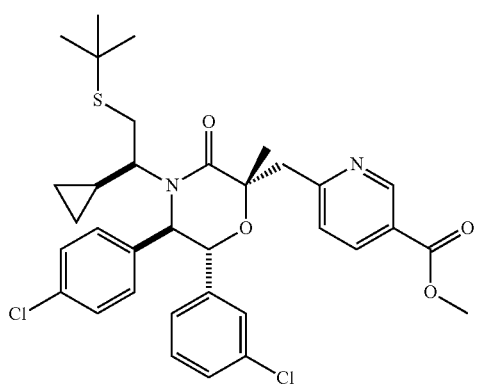 [SMILES: COC(=O)c1ccc(C[C@]2(C)O[C@H](c3cccc(Cl)c3)[C@@H](c3ccc(Cl)cc3)N([C@H](CSC(C)(C)C)C3CC3)C2=O)nc1]

Cyanomethylenetributylphosphorane (0.356 g, 1.48 mmol) and tert-butanethiol (0.133 g, 1.48 mmol) were added to a solution of methyl 6-(((2S,5R,6R)-6-(3-chlorophenyl)-5-(4-chlorophenyl)-4-((S)-1-cyclopropyl-2-hydroxyethyl)-2-methyl-3-oxomorpholin-2-yl)methyl)nicotinate (Example 1, Step G, 210 mg, 0.37 mmol) in toluene (2 mL), and the mixture was stirred at 70° C. overnight. The resulting mixture was cooled and concentrated. Purification of the residue by flash column chromatography (silica gel column, gradient elution of 0% to 35% ethyl acetate in hexanes) afforded the title compound.

MS (ESI) m/z: 641.1 [M+H]$^+$.

Step I. Methyl 6-(((2S,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)methyl)nicotinate

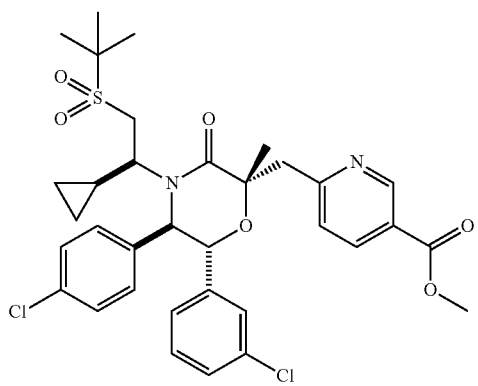 [SMILES: COC(=O)c1ccc(C[C@]2(C)O[C@H](c3cccc(Cl)c3)[C@@H](c3ccc(Cl)cc3)N([C@H](CS(=O)(=O)C(C)(C)C)C3CC3)C2=O)nc1]

3-Chloroperbenzoic acid (77 wt. %, 0.031 g, 0.14 mmol) was added to a solution of methyl 6-(((2S,5R,6R)-4-((S)-2-(tert-butylthio)-1-cyclopropylethyl)-6-(3-chlorophenyl)-5-(4-chlorophenyl)-2-methyl-3-oxomorpholin-2-yl)methyl)nicotinate (Example 1, Step H, 60 mg, 0.07 mmol) in dichloromethane (3 mL) at 0° C. The reaction was quenched after 30 minutes with 1 N sodium thiosulfate (5 mL) and washed with ethyl acetate (3×10 mL). The combined organic layer was dried over magnesium sulfate, filtered and concentrated. Purification of the residue by flash column chromatography (silica gel column, gradient elution of 0% to 40% acetone in hexanes) afforded the title compound.

MS (ESI) m/z: 673.0 [M+H]$^+$.

Step J. 6-(((2S,5R,6R)-4-((S)-2-(tert-Butylsulfonyl)-1-cyclopropylethyl)-6-(3-chlorophenyl)-5-(4-chlorophenyl)-2-methyl-3-oxomorpholin-2-yl)methyl)nicotinic acid

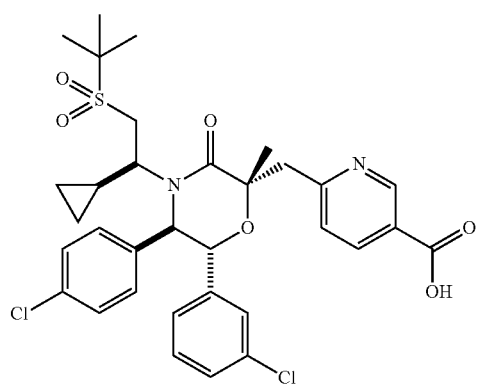 [SMILES: CC(C)(C)S(=O)(=O)C[C@H](C1CC1)N1C(=O)[C@](C)(Cc2ccc(C(=O)O)cn2)O[C@H](c2cccc(Cl)c2)[C@H]1c1ccc(Cl)cc1]

Lithium hydroxide (1 mL, 2 M solution) was added to a solution of methyl 6-(((2S,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)methyl)nicotinate (Example 1, Step I, 30 mg, 0.045 mmol) in methanol (1 mL) and tetrahydrofuran (1 mL) at room temperature. The resulting mixture was heated at 50° C. for 1 hour. The resulting mixture was cooled, quenched with a 10% citric acid solution (5 mL), and extracted with ethyl acetate (3×10 mL). The combined organic layers were dried over magnesium sulfate, filtered and concentrated. Purification of the residue by flash column chromatography (silica gel column, gradient elution of 0% to 100% ethyl acetate in hexanes) afforded the title compound.

$^1$H NMR (400 MHz, CDCl$_3$, δ, ppm): 9.33 (s, 1H), 8.56 (d, J=8.61 Hz, 1H), 7.63 (d, J=8.22 Hz, 1H), 7.19-7.26 (m, 2H), 7.11-7.18 (m, 3H), 7.04 (t, J=8.12 Hz, 2H), 6.82 (d, J=7.63 Hz, 1H), 5.17 (d, J=9.78 Hz, 1H), 5.06 (d, J=9.78 Hz, 1H), 4.15-4.27 (m, J=12.72 Hz, 1H), 3.89 (d, J=13.11 Hz, 2H), 3.72 (d, J=13.30 Hz, 1H), 2.92 (d, J=13.50 Hz, 1H), 2.71 (t, J=9.68 Hz, 1H), 1.81-1.97 (m, 1H), 1.68 (s, 3H), 1.40 (s, 9H), 0.31-0.54 (m, 1H), −0.33 to −0.20 (m, 1H), −0.79 to −0.59 (m, 1H). MS (ESI) m/z: 659.0 [M+H]$^+$.

Example 2

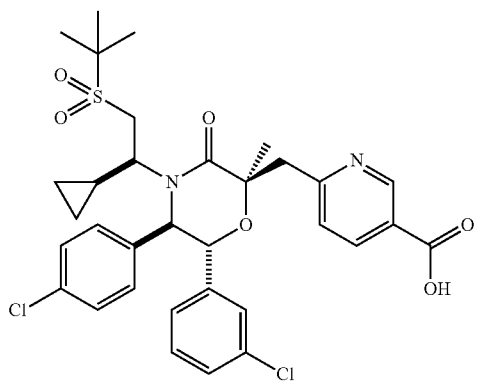 [SMILES: CC(C)(C)S(=O)(=O)C[C@H](C1CC1)N1C(=O)[C@@](C)(Cc2ccc(C(=O)O)cn2)O[C@H](c2cccc(Cl)c2)[C@H]1c1ccc(Cl)cc1]

6-(((2R,5R,6R)-4-((S)-2-(tert-Butylsulfonyl)-1-cyclopropylethyl)-6-(3-chlorophenyl)-5-(4-chlorophenyl)-2-methyl-3-oxomorpholin-2-yl)methyl)nicotinic acid Step A. Methyl 6-(((2R,5R,6R)-6-(3-chlorophenyl)-5-(4-chlorophenyl)-4-((S)-1-cyclopropyl-2-hydroxyethyl)-2-methyl-3-oxomorpholin-2-yl)methyl)nicotinate

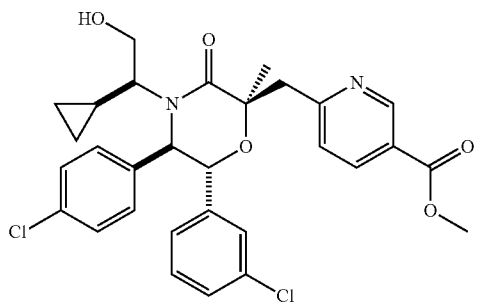 [SMILES: COC(=O)c1ccc(C[C@@]2(C)O[C@H](c3cccc(Cl)c3)[C@@H](c3ccc(Cl)cc3)N([C@H](CO)C3CC3)C2=O)nc1]

The title compound was obtained from methyl 6-(((2R,5R,6R)-4-((S)-2-((tert-butyldimethylsilyl)oxy)-1-cyclopropylethyl)-6-(3-chlorophenyl)-5-(4-chlorophenyl)-2-methyl-3-oxomorpholin-2-yl)methyl)nicotinate (Example 1, Step F, slower eluting isomer) by a procedure similar to that described in Example 1, Step G. Purification of the residue by flash column chromatography (silica gel column, gradient elution of 0% to 25% ethyl acetate in hexanes) afforded the title compound.

$^1$H NMR (400 MHz, CDCl$_3$, δ, ppm): 9.25 (d, J=1.56 Hz, 1H), 8.34 (dd, J=2.15, 8.22 Hz, 1H), 7.36 (d, J=8.22 Hz, 1H), 7.17-7.27 (m, 2H), 7.10 (dd, J=0.98, 1.96 Hz, 2H), 6.95 (t, J=7.83 Hz, 2H), 6.46 (s, 1H), 6.33 (d, J=7.43 Hz, 1H), 4.81 (d, J=9.59 Hz, 1H), 4.53 (d, J=9.78 Hz, 1H), 4.17-4.26 (m, 1H), 4.11 (s, 1H), 3.99 (s, 3H), 3.58 (dd, J=5.09, 11.54 Hz, 1H), 3.22 (d, J=14.48 Hz, 1H), 2.49-2.64 (m, 1H), 1.86 (s, 3H), 0.87 (s, 1H), 0.26-0.49 (m, 2H), −0.15-0.00 (m, 1H), −0.64 to −0.51 (m, 1H). MS (ESI) m/z: 569.2 [M+H]$^+$.

Step B. Methyl 6-(((2R,5R,6R)-4-((S)-2-(tert-butyl-thio)-1-cyclopropylethyl)-6-(3-chlorophenyl)-5-(4-chlorophenyl)-2-methyl-3-oxomorpholin-2-yl)methyl)nicotinate

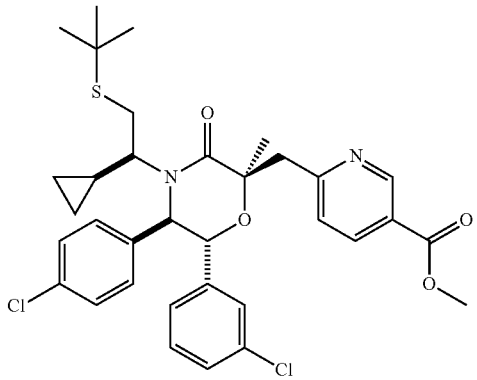 [SMILES: COC(=O)c1ccc(C[C@@]2(C)O[C@H](c3cccc(Cl)c3)[C@@H](c3ccc(Cl)cc3)N([C@H](CSC(C)(C)C)C3CC3)C2=O)nc1]

The title compound was obtained from methyl 6-(((2R,5R,6R)-6-(3-chlorophenyl)-5-(4-chlorophenyl)-4-((S)-1-cyclopropyl-2-hydroxyethyl)-2-methyl-3-oxomorpholin-2-yl)methyl)nicotinate (Example 2, Step A) by a procedure similar to that described in Example 1, Step H. Purification of the residue by flash column chromatography (silica gel column, gradient elution of 0% to 35% ethyl acetate in hexanes) afforded the title compound.

$^1$H NMR (400 MHz, CDCl$_3$, δ, ppm): 9.27 (d, J=1.56 Hz, 1H), 8.17-8.31 (m, 1H), 7.43 (d, J=8.02 Hz, 1H), 7.24 (d, J=7.83 Hz, 2H), 7.12-7.19 (m, 1H), 7.03 (s, 3H), 6.78-6.87 (m, 1H), 6.55 (d, J=7.63 Hz, 1H), 4.80 (d, J=9.59 Hz, 1H), 4.63 (d, J=9.59 Hz, 1H), 3.97 (s, 3H), 3.83 (d, J=13.69 Hz, 1H), 3.35 (d, J=13.69 Hz, 1H), 3.03-3.18 (m, 1H), 2.43-2.58 (m, 1H), 1.79 (s, 3H), 1.27 (s, 9H), 0.46-0.57 (m, 1H), 1.27 (m, 1H), 0.46-0.57 (m, 1H), 0.28-0.43 (m, 1H), 0.02-0.16 (m, 1H), −0.46 to −0.33 (m, 1H). MS (ESI) m/z: 641.2 [M+H]$^+$.

Step C. Methyl 6-(((2R,5R,6R)-4-((S)-2-(tert-butyl-sulfonyl)-1-cyclopropylethyl)-6-(3-chlorophenyl)-5-(4-chlorophenyl)-2-methyl-3-oxomorpholin-2-yl)methyl)nicotinate

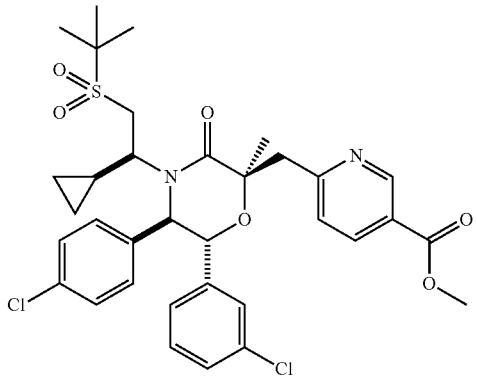 [SMILES: COC(=O)c1ccc(C[C@@]2(C)O[C@H](c3cccc(Cl)c3)[C@@H](c3ccc(Cl)cc3)N([C@H](CS(=O)(=O)C(C)(C)C)C3CC3)C2=O)nc1]

The title compound was obtained from methyl 6-(((2R,5R,6R)-4-((S)-2-(tert-butylthio)-1-cyclopropylethyl)-6-(3-chlorophenyl)-5-(4-chlorophenyl)-2-methyl-3-oxomorpho-lin-2-yl)methyl)nicotinate (Example 2, Step B) by a procedure similar to that described in Example 1, Step I.

Purification of the residue by flash column chromatography (silica gel column, gradient elution of 0% to 40% acetone in hexanes) afforded the title compound.

$^1$H NMR (400 MHz, CDCl$_3$, δ, ppm): 9.29 (s, 1H), 8.23 (d, J=6.26 Hz, 1H), 7.42 (s, 1H), 7.27 (br s, 4H), 7.08-7.15 (m, 1H), 7.01 (t, J=7.83 Hz, 1H), 6.76 (s, 1H), 6.61 (d, J=8.02 Hz, 1H), 4.89 (s, 2H), 3.95 (s, 3H), 3.85 (s, 1H), 3.38 (d, J=14.28 Hz, 1H), 3.23 (d, J=14.28 Hz, 1H), 2.58-2.75 (m, 1H), 1.98-2.13 (m, 1H), 1.77 (s, 3H), 1.53-1.60 (m, 1H), 1.43 (s, 9H), 0.22-0.53 (m, 2H), −0.18-0.01 (m, 1H), −0.62 to −0.40 (m, 1H). MS (ESI) m/z: 673.1 [M+H]$^+$.

Step D. 6-(((2R,5R,6R)-4-((S)-2-(tert-Butylsulfo-nyl)-1-cyclopropylethyl)-6-(3-chlorophenyl)-5-(4-chlorophenyl)-2-methyl-3-oxomorpholin-2-yl)methyl)nicotinic acid

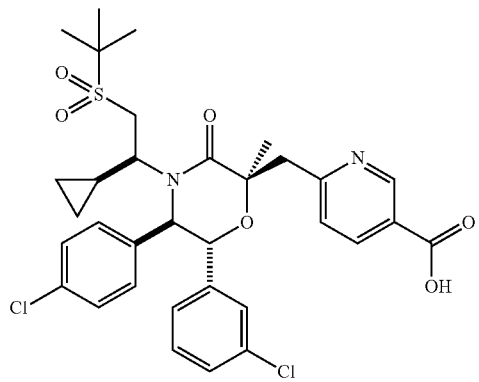 [SMILES: CC(C)(C)S(=O)(=O)C[C@H](C1CC1)N1C(=O)[C@@](C)(Cc2ccc(C(=O)O)cn2)O[C@H](c2cccc(Cl)c2)[C@H]1c1ccc(Cl)cc1]

The title compound was obtained from methyl 6-(((2R,5R,6R)-4-((S)-2-(tert-butylsulfonyl)-1-cyclopropylethyl)-6-(3-chlorophenyl)-5-(4-chlorophenyl)-2-methyl-3-oxomor-pholin-2-yl)methyl)nicotinate (Example 2, Step C) by a procedure similar to that described in Example 1, Step J. Purification of the residue by flash column chromatography (silica gel column, gradient elution of 0% to 100% ethyl acetate in hexanes) afforded the title compound.

$^1$H NMR (400 MHz, CDCl$_3$, δ, ppm): 9.33 (s, 1H), 8.56 (d, J=8.61 Hz, 1H), 7.63 (d, J=8.22 Hz, 1H), 7.27 (br s, 4H), 7.11-7.17 (m, 2H), 7.04 (t, J=8.12 Hz, 1H), 6.82 (d, J=7.63 Hz, 1H), 5.17 (d, J=9.78 Hz, 1H), 5.06 (d, J=9.78 Hz, 1H), 4.13-4.28 (m, J=11.74 Hz, 1H), 3.89 (d, J=13.11 Hz, 1H), 3.72 (d, J=13.30 Hz, 1H), 2.91 (d, J=13.89 Hz, 1H), 2.62-2.79 (m, 1H), 1.80-1.98 (m, 1H), 1.68 (s, 3H), 1.40 (s, 9H), 0.27-0.54 (m, 2H), −0.36 to −0.19 (m, 1H), −0.75 to −0.59 (m, 1H). MS (ESI) m/z: 659.0 [M+H]$^+$.

Example 3

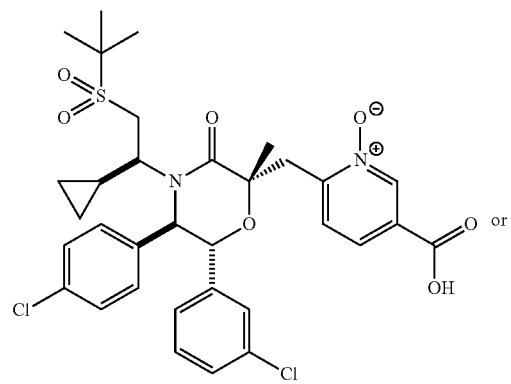

49

-continued

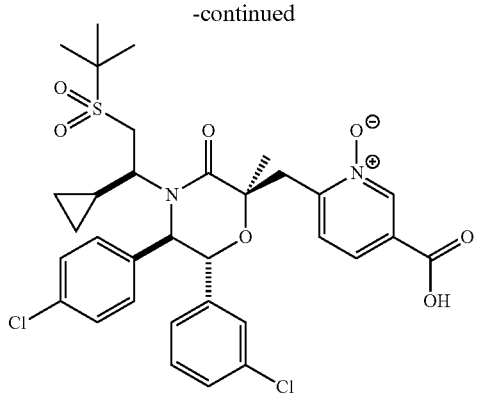

2-(((2S,5R,6R)-4-((S)-2-(tert-Butylsulfonyl)-1-cyclopropylethyl)-6-(3-chlorophenyl)-5-(4-chlorophenyl)-2-methyl-3-oxomorpholin-2-yl)methyl)-5-carboxypyridine 1-oxide or 2-(((2R,5R,6R)-4-((S)-2-(tert-Butylsulfonyl)-1-cyclopropylethyl)-6-(3-chlorophenyl)-5-(4-chlorophenyl)-2-methyl-3-oxomorpholin-2-yl)methyl)-5-carboxypyridine 1-oxide The title compound was obtained from methyl 6-(((2S,5R,6R)-4-((S)-2-((tert-butyldimethylsilyl)oxy)-1-cyclopropylethyl)-6-(3-chlorophenyl)-5-(4-chlorophenyl)-2-methyl-3-oxomorpholin-2-yl)methyl)nicotinate and methyl 6-(((2R,5R,6R)-4-((S)-2-((tert-butyldimethylsilyl)oxy)-1-cyclopropylethyl)-6-(3-chlorophenyl)-5-(4-chlorophenyl)-2-methyl-3-oxomorpholin-2-yl)methyl)nicotinate (Example 1, Step F, diastereomers not separated) by a procedure similar to that described in Example 1, Steps G through J. In Step I, an excess of 3-chloroperbenzoic acid (3 equivalents) is used to promote oxidation of both the sulfide and the pyridine. The resulting product (mixture of C-2 diastereomers) was purified by reverse phase preparatory HPLC (Gemini™ Prep C$_{18}$, 5 µm column; Phenomenex, Torrance, Calif.; gradient elution of 25% to 75% acetonitrile in water, where both solvents contain 0.1% trifluoroacetic acid, 30 minute method) to provide the title compound as the first (faster) eluting isomer.

$^1$H NMR (400 MHz, CDCl$_3$, δ, ppm): 8.92-9.19 (m, 1H), 8.00-8.10 (m, 1H), 7.83 (d, J=7.58 Hz, 1H), 7.17 (d, J=7.82 Hz, 2H), 7.08 (t, J=7.83 Hz, 2H), 6.95 (br s, 2H), 6.79 (d, J=7.34 Hz, 2H), 5.06 (d, J=9.54 Hz, 1H), 4.90 (d, J=10.03 Hz, 1H), 4.22-4.35 (m, J=8.07 Hz, 1H), 4.13 (d, J=13.45 Hz, 1H), 3.71 (d, J=13.20 Hz, 1H), 3.01 (d, J=13.69 Hz, 1H), 2.62-2.74 (m, 1H), 1.90-2.04 (m, 1H), 1.80 (br s, 3H), 1.43 (s, 9H), 0.41 (br s, 2H), −0.23 (br s, 1H), −0.69 (br s, 1H). MS (ESI) m/z: 675.2 [M+H]$^+$.

Example 4

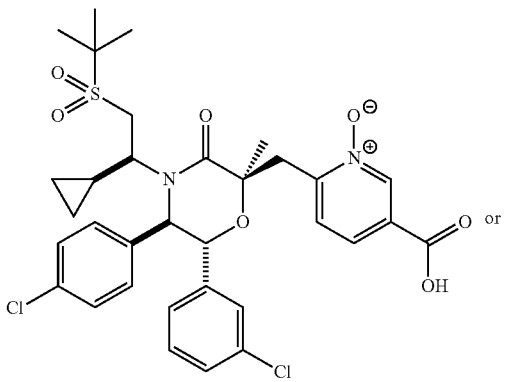

50

-continued

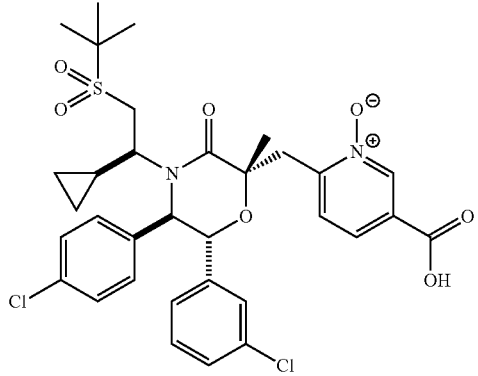

2-(((2R,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)methyl)-5-carboxypyridine 1-oxide or 2-(((2S,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)methyl)-5-carboxypyridine 1-oxide Further elution of Example 3 provided the title compound as the second (slower) eluting isomer.

$^1$H NMR (400 MHz, CDCl$_3$, δ, ppm): 8.99-9.19 (m, 1H), 8.04-8.18 (m, 1H), 7.62 (d, J=7.83 Hz, 1H), 7.14-7.24 (m, 4H), 7.10 (d, J=15.65 Hz, 2H), 6.93 (d, J=6.60 Hz, 2H), 5.42 (d, J=9.05 Hz, 1H), 5.05 (d, J=9.78 Hz, 1H), 4.40 (d, J=11.74 Hz, 1H), 4.11-4.25 (m, J=11.25 Hz, 1H), 3.16 (d, J=11.25 Hz, 1H), 2.88 (d, J=11.49 Hz, 1H), 2.66-2.76 (m, 2H), 1.84 (br s, 1H), 1.72 (br s, 3H), 1.39 (s, 9H), 0.27-0.49 (m, 1H), −0.31 (br s, 1H), −0.84 (br s, 1H). MS (ESI) m/z: 675.2 [M+H]$^+$.

Example 5

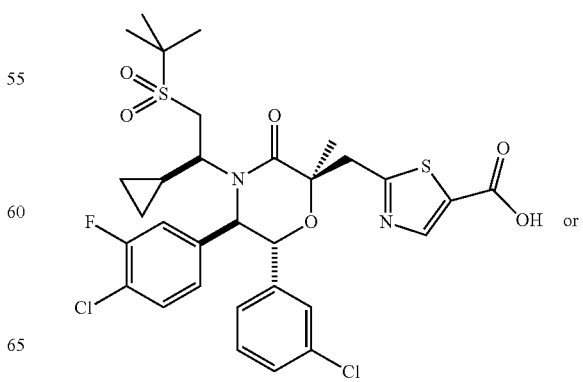

-continued

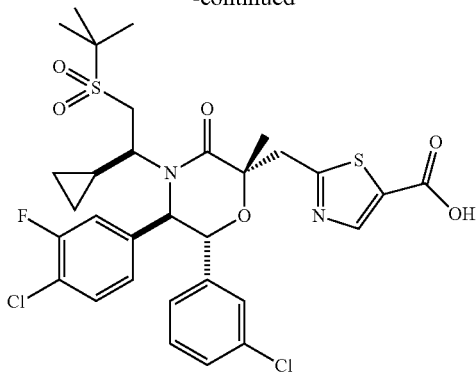

2-(((2R,5R,6R)-4-((S)-2-(tert-Butylsulfonyl)-1-cyclopropylethyl)-5-(4-chloro-3-fluorophenyl)-6-(3-chlorophenyl)-2-methyl-3-oxomorpholin-2-yl)methyl)thiazole-5-carboxylic acid or 2-(((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)thiazole-5-carboxylic acid Step A. (2R,5R,6R)-4-((S)-2-((tert-Butyldimethylsilyl)oxy)-1-cyclopropylethyl)-5-(4-chloro-3-fluorophenyl)-6-(3-chlorophenyl)-2-methylmorpholin-3-one and (2S,5R,6R)-4-((S)-2-((tert-Butyldimethylsilyl)oxy)-1-cyclopropylethyl)-5-(4-chloro-3-fluorophenyl)-6-(3-chlorophenyl)-2-methylmorpholin-3-one

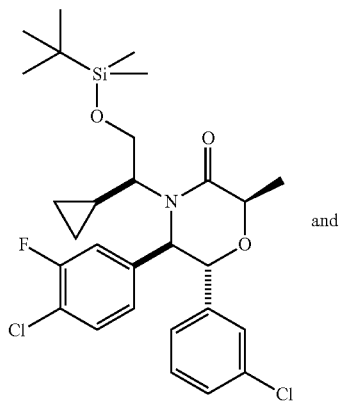

and

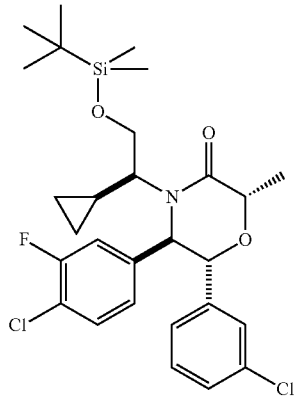

The above compound was prepared from (1R,2R)-2-amino-2-(4-chloro-3-fluorophenyl)-1-(3-chlorophenyl)ethanol (prepared by a method analogous to that described for Intermediate A, using 4-chloro-3-fluorobenzyl bromide in place of 4-chlorobenzyl bromide) using the methods described in Example 1, Steps A through E. Purification of the residue by flash column chromatography (silica gel column, gradient elution of 0% to 20% ethyl acetate in hexanes) afforded the title compounds as a 1:1 mixture of diastereomers. MS (ESI) m/z: 552.2 [M+H]$^+$ for both isomers.

Step B. (2S,5R,6R)-2-Allyl-4-((S)-2-((tert-butyldimethylsilyl)oxy)-1-cyclopropylethyl)-5-(4-chloro-3-fluorophenyl)-6-(3-chlorophenyl)-2-methylmorpholin-3-one and (2R,5R,6R)-2-allyl-4-((S)-2-((tert-butyldimethylsilyl)oxy)-1-cyclopropylethyl)-5-(4-chloro-3-fluorophenyl)-6-(3-chlorophenyl)-2-methylmorpholin-3-one

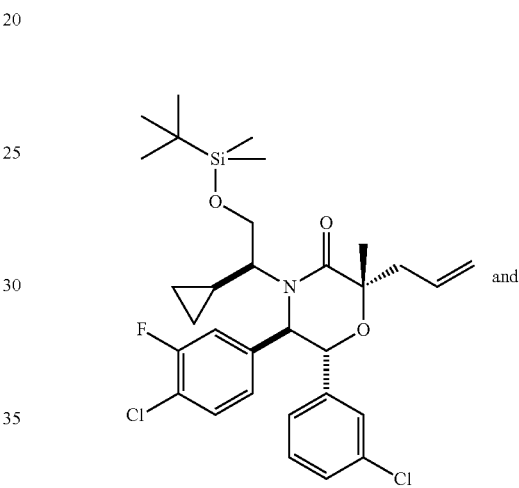

and

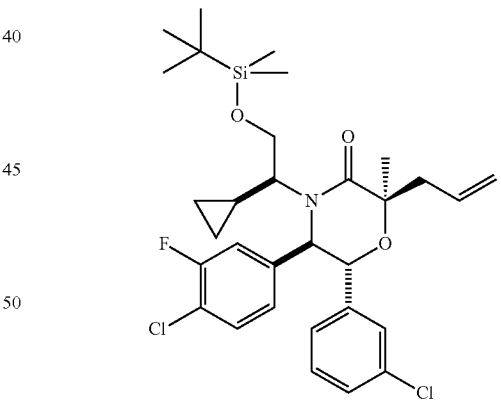

Allyl bromide (0.69 ml, 8.0 mmol) followed by lithium bis(trimethylsilyl)amide (1.0 M solution in tetrahydrofuran, 8.0 ml, 8.0 mmol) was added to a solution of (2R,5R,6R)-4-((S)-2-((tert-butyldimethylsilyl)oxy)-1-cyclopropylethyl)-5-(4-chloro-3-fluorophenyl)-6-(3-chlorophenyl)-2-methylmorpholin-3-one and (2S,5R,6R)-4-((S)-2-((tert-butyldimethylsilyl)oxy)-1-cyclopropylethyl)-5-(4-chloro-3-fluorophenyl)-6-(3-chlorophenyl)-2-methylmorpholin-3-one (Example 5, Step A, 1.1 g, 2.0 mmol) in tetrahydrofuran (2.0 mL) at −78° C. The reaction mixture was stirred at −40° C. over the weekend.

The reaction was quenched with saturated ammonium chloride (10 mL), diluted with brine (30 mL) and extracted with diethyl ether (3×30 mL). The combined organic layer was dried over magnesium sulfate, filtered and concentrated under a vacuum. The resulting material was absorbed onto a plug of silica gel and purified by flash chromatography (silica gel column, 80 g, gradient elution of 0% to 40% acetone in hexanes) afforded the title compounds as light-yellow solid and a nearly 1:1 mixture of diastereomers. MS (ESI) m/z: 592.2 [M−H]+ for both isomers.

Step C. (2S,5R,6R)-2-Allyl-5-(4-chloro-3-fluoro-phenyl)-6-(3-chlorophenyl)-4-((S)-1-cyclopropyl-2-hydroxyethyl)-2-methylmorpholin-3-one and (2R,5R,6R)-2-allyl-5-(4-chloro-3-fluorophenyl)-6-(3-chlorophenyl)-4-((S)-1-cyclopropyl-2-hydroxyethyl)-2-methylmorpholin-3-one

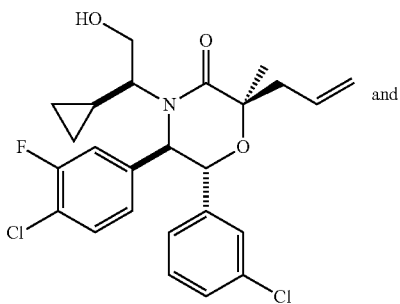
and

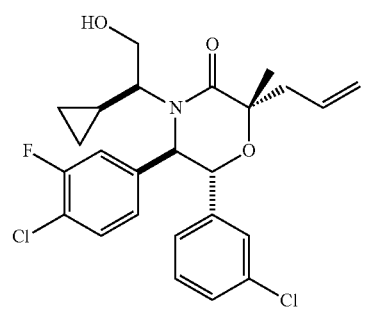

The title compounds were prepared from a mixture of (2S,5R,6R)-2-Allyl-4-((S)-2-((tert-butyldimethylsilyl)oxy)-1-cyclopropylethyl)-5-(4-chloro-3-fluorophenyl)-6-(3-chlorophenyl)-2-methylmorpholin-3-one and (2R,5R,6R)-2-allyl-4-((S)-2-((tert-butyldimethylsilyl)oxy)-1-cyclopropylethyl)-5-(4-chloro-3-fluorophenyl)-6-(3-chlorophenyl)-2-methylmorpholin-3-one (Example 5, Step B) using the method described in Example 1, Step G. Purification of the residue by flash chromatography (silica gel column, gradient elution of 20% to 40% ethyl acetate in hexanes) afforded the title compounds.

Characterization data for faster eluting isomer: (2S,5R,6R)-2-allyl-5-(4-chloro-3-fluorophenyl)-6-(3-chlorophenyl)-4-((S)-1-cyclopropyl-2-hydroxyethyl)-2-methylmorpholin-3-one or (2R,5R,6R)-2-allyl-5-(4-chloro-3-fluorophenyl)-6-(3-chlorophenyl)-4-((5)-1-cyclopropyl-2-hydroxyethyl)-2-methylmorpholin-3-one

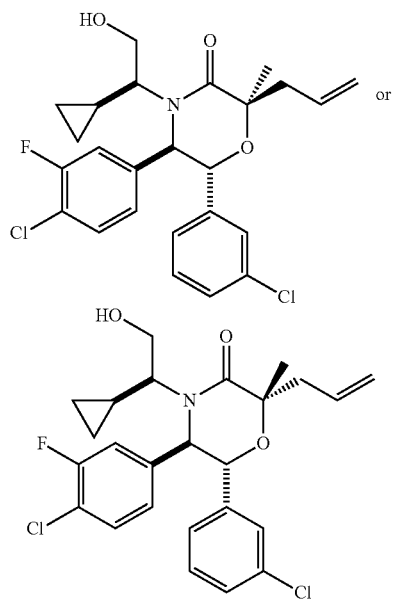

1H NMR (400 MHz, CDCl3, δ, ppm): 7.33 (t, J=7.83 Hz, 1H), 7.25 (dd, J=0.98, 2.20 Hz, 1H), 7.08-7.19 (m, 2H), 6.92 (br s, 2H), 6.69 (d, J=7.83 Hz, 1H), 5.77-5.92 (m, 1H), 5.09-5.25 (m, 2H), 4.86-4.92 (m, 1H), 4.76-4.85 (m, 1H), 3.64 (dd, J=4.77, 11.13 Hz, 1H), 3.39 (dt, J=4.65, 10.39 Hz, 1H), 3.17-3.25 (m, 1H), 3.02 (dd, J=6.36, 14.67 Hz, 1H), 2.66 (dd, J=8.19, 14.79 Hz, 1H), 1.53 (s, 3H), 0.69-0.79 (m, 1H), 0.51-0.68 (m, 2H), 0.20-0.32 (m, 1H), 0.09-0.18 (m, 1H). MS (ESI) m/z: 478.2 [M+H]+.

Characterization data for the slower eluting isomer, (2S,5R,6R)-2-allyl-5-(4-chloro-3-fluorophenyl)-6-(3-chlorophenyl)-4-((S)-1-cyclopropyl-2-hydroxyethyl)-2-methylmorpholin-3-one or (2R,5R,6R)-2-allyl-5-(4-chloro-3-fluorophenyl)-6-(3-chlorophenyl)-4-((S)-1-cyclopropyl-2-hydroxyethyl)-2-methylmorpholin-3-one

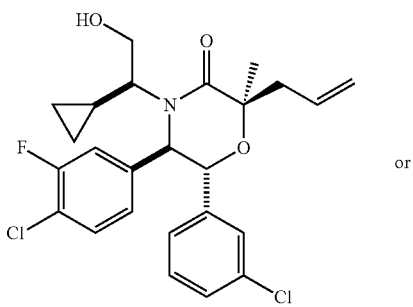

-continued

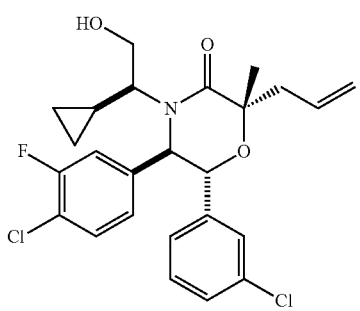

¹H NMR (400 MHz, CDCl₃, δ, ppm): 7.33 (t, J=7.83 Hz, 1H), 7.25 (dd, J=0.98, 2.20 Hz, 1H), 7.08-7.19 (m, 2H), 6.92 (br s, 2H), 6.69 (d, J=7.83 Hz, 1H), 5.77-5.92 (m, 1H), 5.09-5.25 (m, 2H), 4.86-4.92 (m, 1H), 4.76-4.85 (m, 1H), 3.64 (dd, J=4.77, 11.13 Hz, 1H), 3.39 (dt, J=4.65, 10.39 Hz, 1H), 3.17-3.25 (m, 1H), 3.02 (dd, J=6.36, 14.67 Hz, 1H), 2.66 (dd, J=8.19, 14.79 Hz, 1H), 1.53 (s, 3H), 0.69-0.79 (m, 1H), 0.51-0.68 (m, 2H), 0.20-0.32 (m, 1H), 0.09-0.18 (m, 1H). MS (ESI) m/z: 478.2 [M+H]⁺.

Step D. (2R,5R,6R)-2-Allyl-4-((S)-2-(tert-butylthio)-1-cyclopropylethyl)-5-(4-chloro-3-fluorophenyl)-6-(3-chlorophenyl)-2-methylmorpholin-3-one or (2S,5R,6R)-2-allyl-4-((S)-2-(tert-butylthio)-1-cyclopropylethyl)-5-(4-chloro-3-fluorophenyl)-6-(3-chlorophenyl)-2-methylmorpholin-3-one

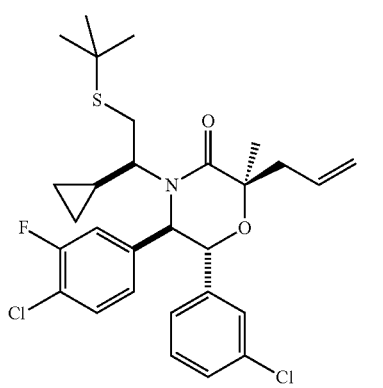

or

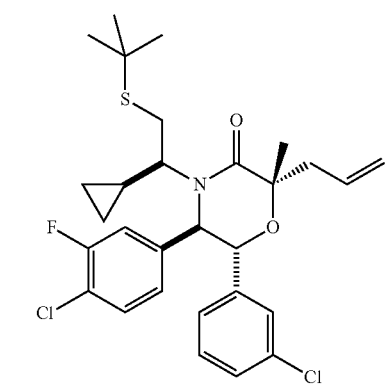

The above compound was prepared from (2S,5R,6R)-2-allyl-5-(4-chloro-3-fluorophenyl)-6-(3-chlorophenyl)-4-((S)-1-cyclopropyl-2-hydroxyethyl)-2-methylmorpholin-3-one or (2R,5R,6R)-2-allyl-5-(4-chloro-3-fluorophenyl)-6-(3-chlorophenyl)-4-((S)-1-cyclopropyl-2-hydroxyethyl)-2-methylmorpholin-3-one (Example 5, Step C, slowest eluting isomer) using the methods described in Example 1, Step H. Purification of the residue by flash column chromatography (silica gel column, eluting with 0% to 40% acetone in hexanes) afforded one of the title compounds. MS (ESI) m/z: 550.2 [M+H]⁺.

Step E. (2-((2R,5R,6R)-4-((S)-2-(tert-Butylsulfonyl)-1-cyclopropylethyl)-5-(4-chloro-3-fluorophenyl)-6-(3-chlorophenyl)-2-methyl-3-oxomorpholin-2-yl)acetic acid or (2-((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)acetic acid

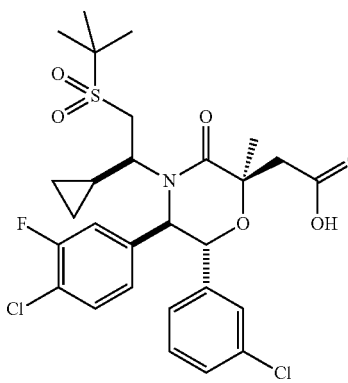

or

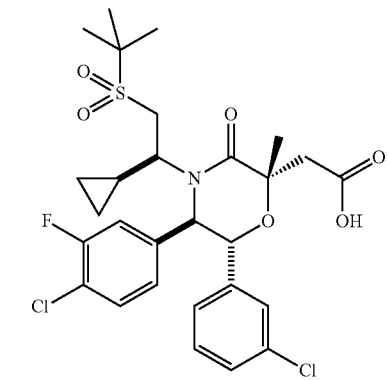

Sodium periodate (280 mg, 1.31 mmol) and ruthenium (III) chloride hydrate (4.91 mg, 0.022 mmol) were sequentially added to a rapidly stirring solution of (2R,5R,6R)-2-allyl-4-((S)-2-(tert-butylthio)-1-cyclopropylethyl)-5-(4-chloro-3-fluorophenyl)-6-(3-chlorophenyl)-2-methylmorpholin-3-one or (2S,5R,6R)-2-allyl-4-((S)-2-(tert-butylthio)-1-cyclopropylethyl)-5-(4-chloro-3-fluorophenyl)-6-(3-chlorophenyl)-2-methylmorpholin-3-one (Example 5, Step D, 120 mg, 0.218 mmol) in water (1.9 mL), acetonitrile (1.2 mL) and carbon tetrachloride (1.2 mL). After stirring vigorously for 1 hour, the reaction was acidified with 10% citric acid (1 mL) and diluted with ethyl acetate (10 mL). The mixture was stirred for 5 minutes, and the resulting solution was transferred to a separation funnel, diluted with brine (1 mL) and the layers were separated. The aqueous layer was washed twice with ethyl acetate (2×10 mL) and the combined organic layer was washed with brine (20 mL), dried over sodium sulfate, and concentrated under reduced pressure. This material was taken to the next step without further purification. MS (ESI) m/z: 600.0 [M+H]⁺.

Step F. 2-((2R,5R,6R)-4-((S)-2-(tert-Butylsulfonyl)-1-cyclopropylethyl)-5-(4-chloro-3-fluorophenyl)-6-(3-chlorophenyl)-2-methyl-3-oxomorpholin-2-yl)acetamide or 2-((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)acetamide

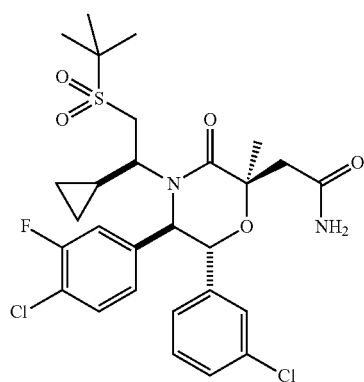

or

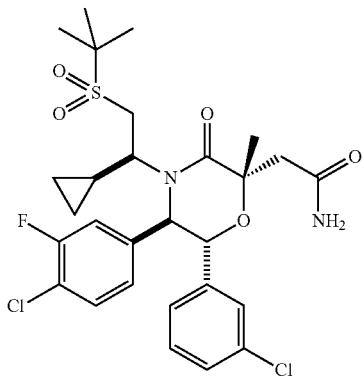

Ammonia (7 N solution in methanol, 0.156 mL, 1.09 mmol) was added to a solution of (2-((2R,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)acetic acid or (2-((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)acetic acid (Example 5, Step E, 131 mg, 0.218 mmol), O-(7-azabenzotriazol-1-yl)-N,N,N',N'-tetramethyluronium hexafluorophosphate (HATU, 166 mg, 0.436 mmol) and N,N-diisopropylethylamine (0.114 mL, 0.655 mmol) in DMF (1.09 mL). After stirring at 40° C. for 1 hour, the resulting material was concentrated. Purification of the residue by flash column chromatography (silica gel column, gradient elution of 0% to 40% acetone:methanol (9:1) in dichloromethane) afforded one of the title compounds. MS (ESI) m/z: 599.1 [M+H]⁺.

Step G. 2-((2R,5R,6R)-4-((S)-2-(tert-Butylsulfonyl)-1-cyclopropylethyl)-5-(4-chloro-3-fluorophenyl)-6-(3-chlorophenyl)-2-methyl-3-oxomorpholin-2-yl)acetonitrile or 2-((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)acetonitrile

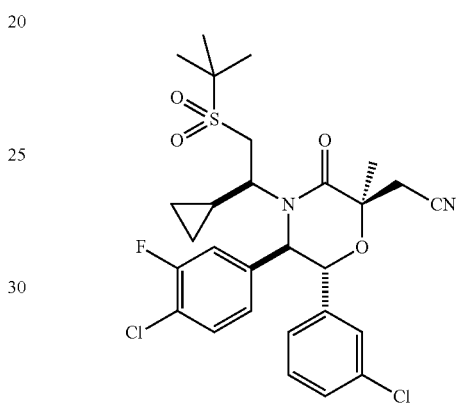

or

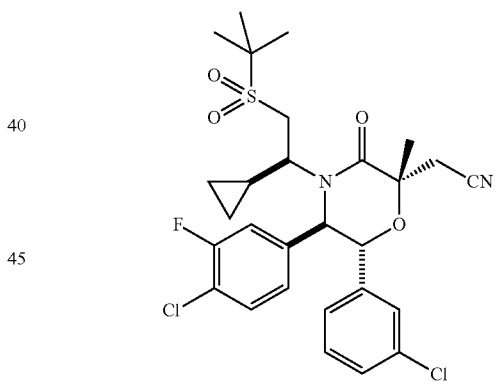

Trifluoroacetic acid anhydride (0.056 mL, 0.400 mmol) was added to a solution of 2-((2R,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)acetamide or 2-((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)acetamide (Example 5, Step F, 80 mg, 0.133 mmol) and triethylamine (0.093 mL, 0.67 mmol) in tetrahydrofuran (2.7 mL) at 0° C. After stirring for 1 hour, the mixture was concentrated. The resulting product was purified by flash column chromatography (silica gel column, 40 g, gradient elution of 0% to 50% acetone in hexanes) to give one of the title compounds. MS (ESI) m/z: 581.0 [M+H]⁺.

Step H. 2-((2R,5R,6R)-4-((S)-2-(tert-Butylsulfonyl)-1-cyclopropylethyl)-5-(4-chloro-3-fluorophenyl)-6-(3-chlorophenyl)-2-methyl-3-oxomorpholin-2-yl)ethanethioamide or 2-((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)ethanethioamide Step I. Ethyl 2-(((2R,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)thiazole-5-carboxylate or ethyl 2-(((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)thiazole-5-carboxylate

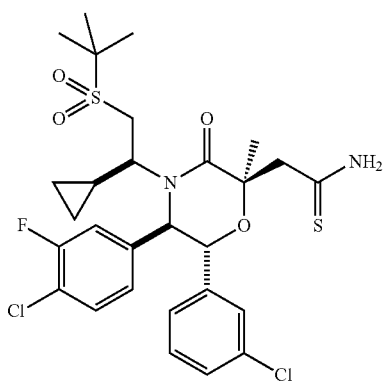

or

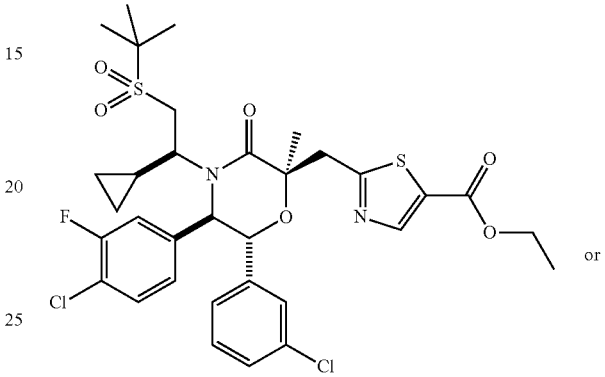

or

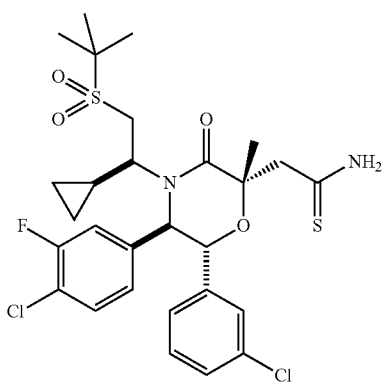

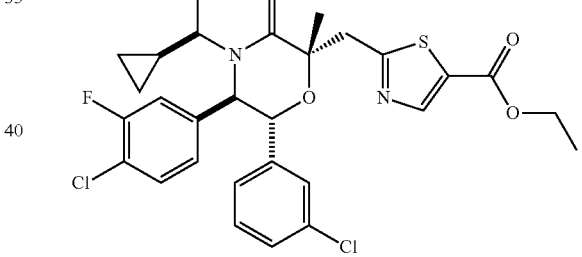

Diphosphorous pentasulfide (122 mg, 0.550 mmol) was added to a solution of 2-((2R,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)acetonitrile or 2-((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)acetonitrile (Example 5, Step G, 80 mg, 0.138 mmol) in ethanol (688 µL), and the reaction was stirred at 70° C. overnight. The resulting material was concentrated and absorbed onto a plug of silica gel and purified by flash column chromatography (silica gel column, 40 g, gradient elution of 0% to 100% acetone in dichloromethane) to provide one of the title compounds. MS (ESI) m/z: 615.0 [M+H]$^+$.

In a microwave vessel, a solution of 2-((2R,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)ethanethioamide or 2-((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)ethanethioamide (Example 5, Step H, 65 mg, 0.106 mmol) in toluene (1 mL) and ethyl 2-chloro-3-oxopropanoate (Accela ChemBio Inc., San Diego, Calif. 31.8 mg, 0.211 mmol) in toluene (1 mL) were combined and stirred at 100° C. in the microwave.

After for 4 hours the resulting material was cooled, concentrated under a vacuum, and absorbed onto a plug of silica gel and purified by flash column chromatography (silica gel column, 40 g, gradient elution of 0% to 40% acetone in dichloromethane) to provide one of the title compounds. MS (ESI) m/z: 711.0 [M+H]$^+$.

Step J. 2-(((2R,5R,6R)-4-((S)-2-(tert-Butylsulfonyl)-1-cyclopropylethyl)-5-(4-chloro-3-fluorophenyl)-6-(3-chlorophenyl)-2-methyl-3-oxomorpholin-2-yl)methyl)thiazole-5-carboxylic acid or 2-(((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)thiazole-5-carboxylic acid

Example 6

6-(((2R,5R,6R)-4-((S)-2-(tert-Butylsulfonyl)-1-cyclopropylethyl)-5-(4-chloro-3-fluorophenyl)-6-(3-chlorophenyl)-2-methyl-3-oxomorpholin-2-yl)methyl)nicotinic acid or 6-(((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)nicotinic acid

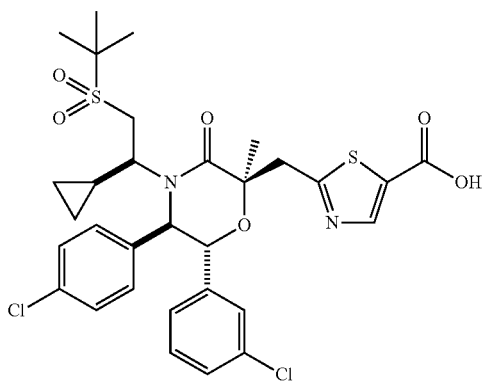

or

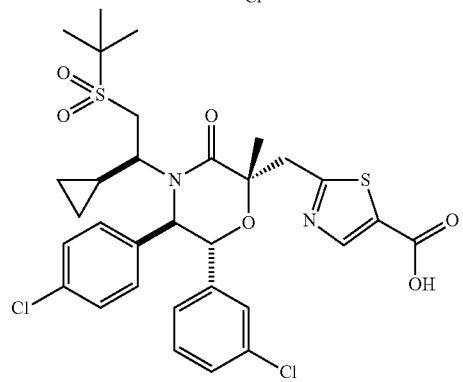

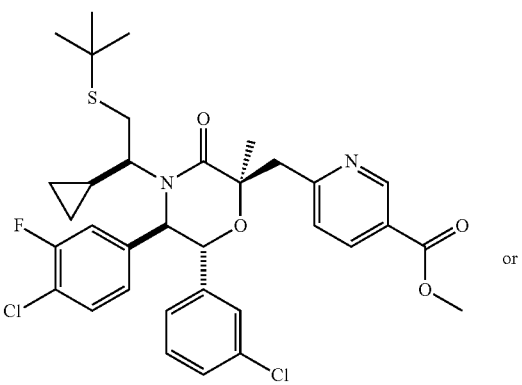

or

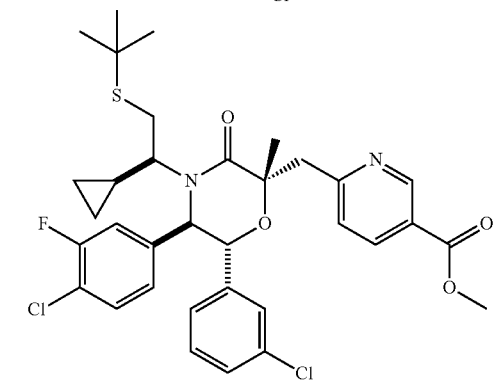

The title compound was synthesized from ethyl 2-(((2R,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)thiazole-5-carboxylate or ethyl 2-(((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)thiazole-5-carboxylate (Example 5, Step I) by procedures similar to those described in Example A, Step J. The resulting product was purified by reverse phase preparatory HPLC (Gemini™ Prep $C_{18}$, 5 μm column; Phenomenex, Torrance, Calif.; gradient elution of 25% to 75% acetonitrile in water, where both solvents contain 0.1% trifluoroacetic acid, 30 minute method) to provide one of the title compound ($t_R$=19.0 minutes) as a white foam.

$^1$H NMR (400 MHz, CDCl$_3$, δ, ppm): 8.43 (s, 1H), 7.29-7.35 (m, 2H), 7.05-7.22 (m, 3H), 6.95-7.05 (m, 1H), 6.88 (br s, 1H), 6.81 (s, 1H), 5.11 (d, J=9.39 Hz, 1H), 4.79 (d, J=9.59 Hz, 1H), 4.27 (t, J=11.44 Hz, 1H), 3.98 (d, J=14.67 Hz, 1H), 3.73 (d, J=14.48 Hz, 1H), 2.98 (br s, 2H), 2.68 (br s, 1H), 2.02 (br s, 1H), 1.69 (s, 3H), 1.32-1.50 (m, 9H), 0.48 (br s, 2H), −0.20 (br s, 1H), −0.65 (br s, 1H). MS (ESI) m/z: 683.0 [M+H]$^+$.

Step A. Methyl 6-(((2R,5R,6R)-5-(4-chloro-3-fluorophenyl)-6-(3-chlorophenyl)-4-((S)-1-cyclopropyl-2-hydroxyethyl)-2-methyl-3-oxomorpholin-2-yl)methyl)nicotinate and methyl 6-(((2S,5R,6R)-5-(4-chloro-3-fluorophenyl)-6-(3-chlorophenyl)-4-((S)-1-cyclopropyl-2-hydroxyethyl)-2-methyl-3-oxomorpholin-2-yl)methyl)nicotinate

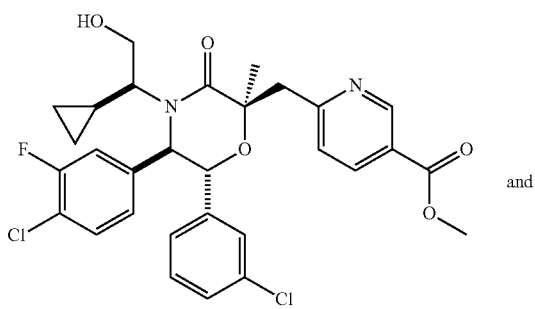

and

-continued

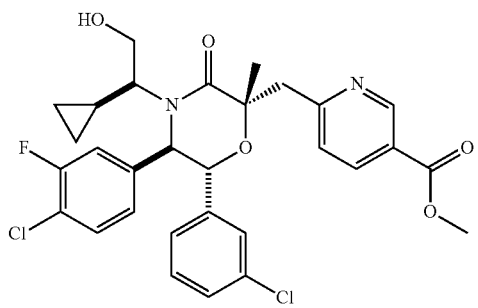

The title compounds were prepared from (1R,2R)-2-amino-2-(4-chloro-3-fluorophenyl)-1-(3-chlorophenyl)ethanol (prepared by a method analogous to that described for Intermediate A substituting 4-chloro-3-fluorobenzyl bromide for 4-chlorobenzyl bromide) using the procedures described in Example 1, Steps A through G. Purification of the residue by flash column chromatography (silica gel column, gradient elution of 0% to 25% ethyl acetate in hexanes) afforded the title compounds Characterization of the faster eluting isomer:
methyl 6-(((2R,5R,6R)-5-(4-chloro-3-fluorophenyl)-6-(3-chlorophenyl)-4-((S)-1-cyclopropyl-2-hydroxyethyl)-2-methyl-3-oxomorpholin-2-yl)methyl)nicotinate or methyl 6-(((2S,5R,6R)-5-(4-chloro-3-fluorophenyl)-6-(3-chlorophenyl)-4-((S)-1-cyclopropyl-2-hydroxyethyl)-2-methyl-3-oxomorpholin-2-yl)methyl)nicotinate

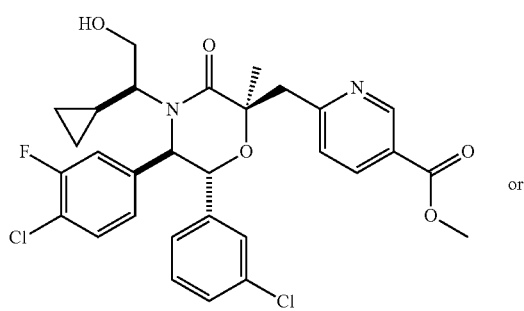

or

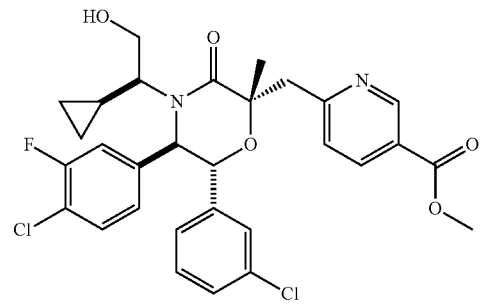

$^1$H NMR (400 MHz, CDCl$_3$, δ, ppm): 9.22-9.26 (m, 1H), 8.35 (dd, J=2.15, 8.02 Hz, 1H), 7.36 (d, J=8.02 Hz, 1H), 7.27 (s, 3H), 7.12 (dd, J=0.98, 1.96 Hz, 1H), 6.98 (t, J=7.92 Hz, 1H), 6.48 (s, 1H), 6.36 (d, J=7.63 Hz, 1H), 4.79 (d, J=9.59 Hz, 1H), 4.56 (d, J=9.59 Hz, 1H), 4.28 (t, J=10.27 Hz, 1H), 4.14 (d, J=14.67 Hz, 1H), 3.99 (s, 3H), 3.59 (dd, J=4.89, 11.74 Hz, 1H), 3.21 (d, J=14.7 Hz, 1H), 2.39-2.58 (m, 1H), 1.86 (s, 3H), 1.49-1.71 (br s, 1H), 1.30-1.45 (m, 1H), 0.32-0.50 (m, 2H), −0.16-0.01 (m, 1H), −0.68 to −0.50 (m, 1H). MS (ESI) m/z: 587.2 [M+H]$^+$.

Characterization of the slower eluting isomer:
methyl 6-(((2R,5R,6R)-5-(4-chloro-3-fluorophenyl)-6-(3-chlorophenyl)-4-((S)-1-cyclopropyl-2-hydroxyethyl)-2-methyl-3-oxomorpholin-2-yl)methyl)nicotinate or methyl 6-(((2S,5R,6R)-5-(4-chloro-3-fluorophenyl)-6-(3-chlorophenyl)-4-((S)-1-cyclopropyl-2-hydroxyethyl)-2-methyl-3-oxomorpholin-2-yl)methyl)nicotinate

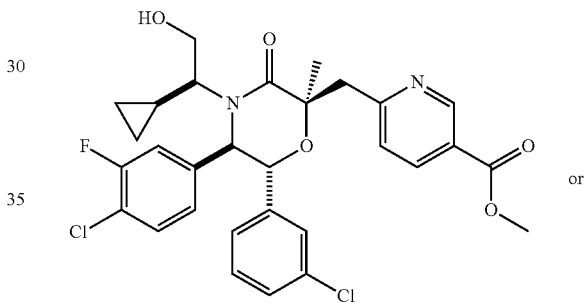

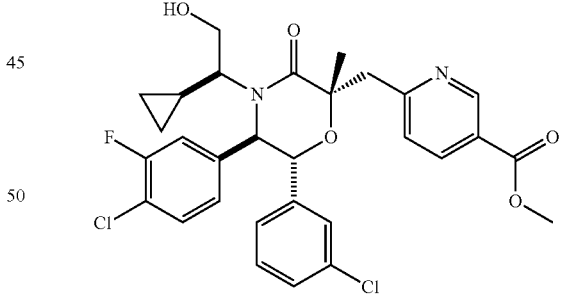

$^1$H NMR (400 MHz, CDCl$_3$, δ, ppm): 9.12 (dd, J=0.78, 2.15 Hz, 1H), 8.22 (dd, J=2.15, 8.02 Hz, 1H), 7.28-7.33 (m, 1H), 7.20-7.26 (m, 2H), 7.14 (t, J=1.76 Hz, 1H), 7.10 (t, J=7.92 Hz, 1H), 6.81 (d, J=19.56 Hz, 2H), 6.63 (d, J=7.63 Hz, 1H), 4.85-4.90 (m, 1H), 4.77-4.81 (m, 1H), 3.95 (s, 3H), 3.82 (d, J=13.69 Hz, 1H), 3.63 (dd, J=4.60, 10.86 Hz, 1H), 3.41 (d, J=13.69 Hz, 2H), 3.19-3.29 (m, 1H), 1.61 (s, 3H), 0.71-0.84 (m, 1H), 0.51-0.70 (m, 3H), 0.20-0.30 (m, 1H), 0.03-0.15 (m, 1H). MS (ESI) m/z: 587.2 [M+H]$^+$.

Step B. Methyl 6-(((2R,5R,6R)-4-((S)-2-(tert-butyl-thio)-1-cyclopropylethyl)-5-(4-chloro-3-fluorophe-nyl)-6-(3-chlorophenyl)-2-methyl-3-oxomorpholin-2-yl)methyl)nicotinate or methyl 6-(((2S,5R,6R)-4-((S)-2-(tert-butylthio)-1-cyclopropylethyl)-5-(4-chloro-3-fluorophenyl)-6-(3-chlorophenyl)-2-methyl-3-oxomorpholin-2-yl)methyl)nicotinate Step C. 6-(((2R,5R,6R)-4-((S)-2-(tert-Butylsulfo-nyl)-1-cyclopropylethyl)-5-(4-chloro-3-fluorophe-nyl)-6-(3-chlorophenyl)-2-methyl-3-oxomorpholin-2-yl)methyl)nicotinic acid or 6-(((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)nicotinic acid

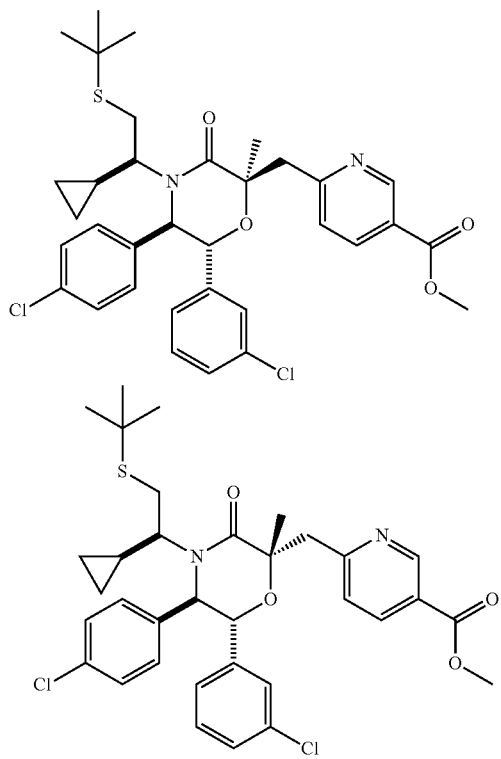

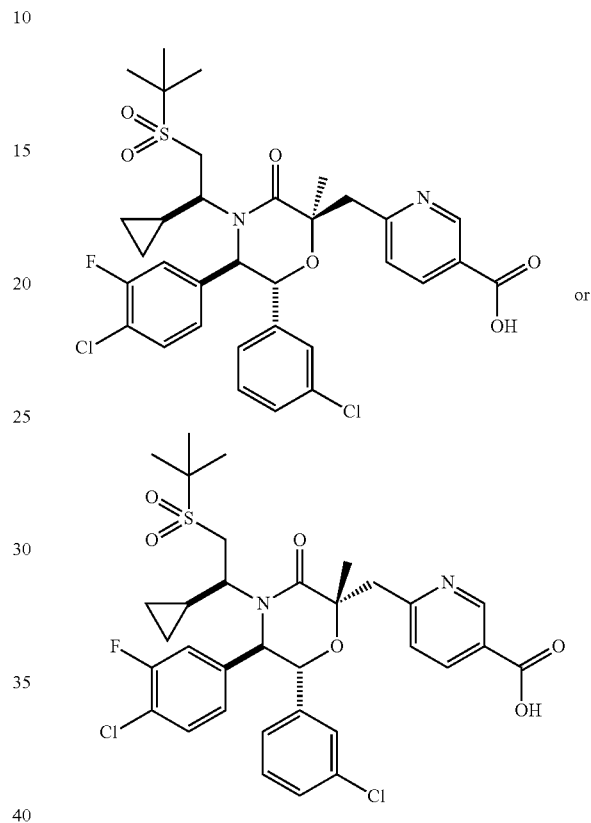

One of the title compounds was prepared from methyl 6-(((2R,5R,6R)-5-(4-chloro-3-fluorophenyl)-6-(3-chloro-phenyl)-4-((S)-1-cyclopropyl-2-hydroxyethyl)-2-methyl-3-oxomorpholin-2-yl)methyl)nicotinate or methyl 6-(((2S,5R,6R)-5-(4-chloro-3-fluorophenyl)-6-(3-chlorophenyl)-4-((S)-1-cyclopropyl-2-hydroxyethyl)-2-methyl-3-oxomorpholin-2-yl)methyl)nicotinate (Example 6, Step A, faster eluting isomer) using the methods described in Example 1, Step H. Purification of the residue by column chromatography (silica gel column, gradient elution of 0% to 40% ethyl acetate in hexanes) afforded one of the title compounds.

$^1$H NMR (400 MHz, CDCl$_3$, δ, ppm): 9.25-9.30 (m, 1H), 8.29 (d, J=7.24 Hz, 1H), 7.45 (d, J=8.22 Hz, 1H), 7.27-7.33 (m, 1H), 7.15-7.22 (m, 1H), 7.07 (t, J=7.83 Hz, 1H), 6.89-6.99 (m, 1H), 6.85-6.88 (m, 1H), 6.68-6.84 (m, 1H), 6.60 (d, J=7.63 Hz, 1H), 4.74-4.80 (m, 1H), 4.62-4.71 (m, 1H), 3.98 (s, 3H), 3.85 (d, J=13.89 Hz, 1H), 3.38 (d, J=13.69 Hz, 1H), 3.06-3.21 (m, 1H), 2.76 (br s, 1H), 2.55 (dd, J=6.16, 12.23 Hz, 1H), 1.79 (s, 3H), 1.28 (s, 9H), 0.89-1.06 (m, 1H), 0.49-0.59 (m, 1H), 0.33-0.47 (m, 1H), 0.03-0.17 (m, 1H), −0.47 to −0.32 (m, 1H). MS (ESI) m/z: 659.0 [M+H]$^+$.

One of the title compounds was prepared from methyl 6-(((2R,5R,6R)-4-((S)-2-(tert-butylthio)-1-cyclopropyl-ethyl)-5-(4-chloro-3-fluorophenyl)-6-(3-chlorophenyl)-2-methyl-3-oxomorpholin-2-yl)methyl)nicotinate or methyl 6-(((2S,5R,6R)-4-((S)-2-(tert-butylthio)-1-cyclopropyl-ethyl)-5-(4-chloro-3-fluorophenyl)-6-(3-chlorophenyl)-2-methyl-3-oxomorpholin-2-yl)methyl)nicotinate (Example 6, Step B) using the methods described in Example 1, Steps I and J. The resulting product was purified by reverse phase preparatory HPLC (Gemini™ Prep C$_{18}$, 5 µm column; Phenomenex, Torrance, Calif.; gradient elution of 25% to 75% acetonitrile in water, where both solvents contain 0.1% trifluoroacetic acid, 30 minute method) to provide one of the title compounds.

$^1$H NMR (400 MHz, CDCl$_3$, δ, ppm): 9.47 (br s, 1H), 8.75 (d, J=8.02 Hz, 1H), 7.94 (d, J=7.82 Hz, 1H), 7.03-7.26 (m, 5H), 6.96 (s, 1H), 6.87 (d, J=7.24 Hz, 1H), 5.02 (d, J=9.19 Hz, 1H), 4.86 (d, J=9.59 Hz, 1H), 4.09-4.28 (m, 1H), 3.99 (d, J=13.89 Hz, 1H), 3.67 (d, J=13.69 Hz, 1H), 2.94 (d, J=13.30 Hz, 1H), 2.45-2.63 (m, 1H), 1.90-2.02 (m, 1H), 1.82 (s, 3H), 1.36 (s, 9H), 0.31-0.56 (m, 2H), −0.32 to −0.15 (m, 1H), −0.71 to −0.57 (m, 1H). MS (ESI) m/z: 677.0 [M+H]$^+$.

Example 7

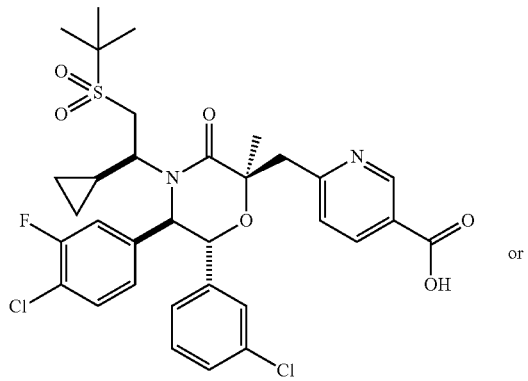

or

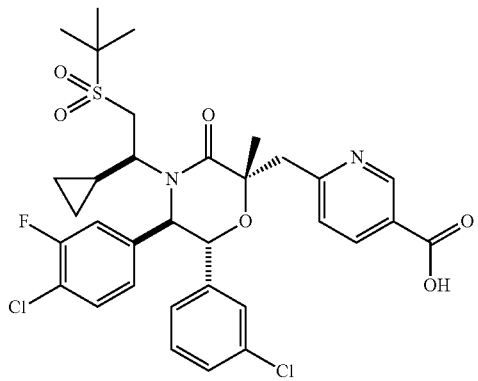

6-(((2R,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)nicotinic acid or 6-(((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)nicotinic acid One of the title compounds was prepared from methyl 6-(((2R,5R,6R)-5-(4-chloro-3-fluorophenyl)-6-(3-chlorophenyl)-4-((S)-1-cyclopropyl-2-hydroxyethyl)-2-methyl-3-oxomorpholin-2-yl)methyl)nicotinate or methyl 6-(((2S,5R,6R)-5-(4-chloro-3-fluorophenyl)-6-(3-chlorophenyl)-4-((S)-1-cyclopropyl-2-hydroxyethyl)-2-methyl-3-oxomorpholin-2-yl)methyl)nicotinate (Example 6, Step A, slower eluting isomer) using the procedures described in Example 6, Steps B and C. The resulting product was purified by reverse phase preparatory HPLC (Gemini™ Prep $C_{18}$, 5 μm column; Phenomenex, Torrance, Calif.; gradient elution of 25% to 75% MeCN in water, where both solvents contain 0.1% trifluoroacetic acid, 30 minute method) to provide one of the title compounds.

$^1$H NMR (500 MHz, CDCl$_3$, δ, ppm): 9.19-9.49 (m, 1H), 8.54-8.72 (m, 1H), 7.67 (d, J=8.31 Hz, 1H), 7.30-7.47 (m, 1H), 7.13-7.23 (m, 3H), 7.07 (t, J=7.95 Hz, 2H), 6.85 (d, J=7.34 Hz, 1H), 5.19 (d, J=9.54 Hz, 1H), 5.07 (d, J=9.54 Hz, 1H), 4.20 (t, J=11.25 Hz, 1H), 3.95 (d, J=12.47 Hz, 1H), 3.71 (d, J=13.20 Hz, 1H), 2.91 (d, J=13.94 Hz, 1H), 2.65-2.77 (m, 1H), 1.84-1.99 (m, 1H), 1.68 (s, 3H), 1.40 (s, 10H), 0.32-0.65 (m, 1H), −0.24 (br s, 1H), −0.63 (br s, 1H). MS (ESI) m/z: 677.0 [M+H]$^+$.

Biological Assays

Compounds of the present invention display inhibition of the interaction between HDM2 and p53 in the following assays.

Homogenous Time-Resolved Fluorescence Assay (HTRF1 Assay)

The standard assay conditions for the in vitro HTRF assay consisted of a 50 ul total reaction volume in black 384-well Costar polypropylene plates in 1×PBS buffer pH 7.4, 1 mM DTT, 0.1% BSA, 2.5 nM GST-hMDM2 (aa 1-188), 5 nM biotinylated-p53 (aa 1-83), 1.8 nM SA-XLent (Cisbio; Bedford, Mass.), 0.6 nM anti-GST cryptate monoclonal antibody (Cisbio; Bedford, Mass.) and 200 mM KF. Amino acid residues 1-188 of human MDM2 were expressed as an amino-terminal glutathione-S-transferase (GST) fusion protein (GST-hMDM2) in *Escherichia coli*. Residues 1-83 of human p53 were expressed as an amino-terminal AviTag™-TrxA-6×His fusion protein (biotinylated p53) in *E. coli*. Each protein was purified from cell paste by affinity chromatography.

Specifically, 10 uL of GST-hMDM2 was incubated with 10 ul of diluted compound (various concentrations, serially diluted) in 10% DMSO for 20 minutes at room temperature. 20 uL of biotinylated-p53 was added to the GST-hMDM2+ compound mixture, and then incubated at room temperature for 60 min. 10 uL of detection buffer consisting of SA-XLent, anti-GST cryptate antibody and KF was added to GST-hMDM2, biotinylated-p53 and compound reaction and left at room temperature to reach equilibrium for >4 hrs. The final concentration of DMSO in the reaction was 2%. Time-resolved fluorescence readings were measured on a microplate multilabel reader. Percentage of inhibition was calculated relative to nutlin-3.

As the potencies of the HDM2 inhibitors increased, an improved HTRF assay (HTRF2 assay) was developed. All assay conditions remained the same as described above, with the exception of the following changes in reagent concentrations: 0.2 nM GST-hMDM2 (1-188), 0.5 nM biotinylated-p53 (1-83), 0.18 nM SA-XLent, and 100 mM KF. Results are provided in the table below.

| Example No. | HTRF2 IC$_{50}$ (μM) |
|---|---|
| 1 | <0.0001 |
| 2 | 0.00014 |
| 3 | 0.00023 |
| 4 | 0.00185 |
| 5 | 0.000121 |
| 6 | 0.00011 |
| 7 | <0.0001 |

What is claimed is:

1. A compound of Formula I, or a pharmaceutically acceptable salt thereof,

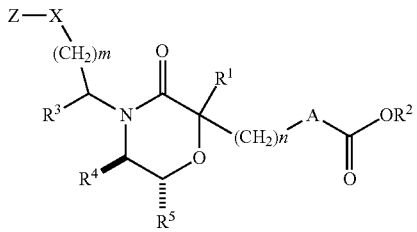

I wherein:
X is S(=O)$_2$ or —S(=O)$_2$N(R$^a$)—;
Z is C$_{1-6}$alkyl or C$_{3-6}$cycloalkyl;
A is a 5 or 6 membered heteroaryl group containing a nitrogen atom, or an N-oxide thereof, and from 0 to 2 additional heteroatoms independently selected from O, N, or S, where the heteroaryl group may be unsubstituted or substituted with from 1 to 3 substituents independently selected from, halo, C$_{1-6}$alkyl, —OC$_{1-6}$alkyl, —OCF$_3$, —CF$_3$, —CHF$_2$ or —CH$_2$F;
R$^1$ is hydrogen or C$_{1-6}$alkyl, where the alkyl group can be unsubstituted or substituted with from 1 to 3 substituents independently selected from halo, —OH, —OC$_{1-6}$alkyl, —OCF$_3$, —CF$_3$, —CN, —CHF$_2$ or —CH$_2$F;
R$^2$ is hydrogen or C$_{1-6}$alkyl;
R$^3$ is C$_{3-6}$cycloalkyl or C$_{1-6}$alkyl, where the cycloalkyl or alkyl group can be unsubstituted or substituted with from 1 to 2 substituents independently selected from halo, C$_{1-6}$alkyl, —CH$_2$CF$_3$, —CF$_3$, —OCF$_3$, —CHF$_2$ or —CH$_2$F;
R$^4$ is a phenyl or pyridyl group which is substituted with from one to three substituents independently selected from halo or C$_{1-6}$ alkyl;
R$^5$ is a phenyl or pyridyl group which is substituted with from one to three substituents independently selected from halo or C$_{1-6}$ alkyl;
n is 0, 1 or 2;
m is 1 or 2; and
R$^a$ is hydrogen, C$_{1-6}$alkyl, C$_{3-6}$cycloalkyl or phenyl, where the phenyl or cycloalkyl group is unsubstituted or substituted with from one to three halo groups.

2. The compound of claim 1, or a pharmaceutically acceptable salt thereof, wherein X is S(=O)$_2$.

3. The compound of claim 1, or a pharmaceutically acceptable salt thereof, wherein X is —S(=O)$_2$N(R$^a$)—.

4. The compound of claim 1, or a pharmaceutically acceptable salt thereof, wherein m is 1.

5. The compound of claim 1, or a pharmaceutically acceptable salt thereof, wherein m is 2.

6. The compound of claim 1, or a pharmaceutically acceptable salt thereof, wherein R$^1$ is hydrogen.

7. The compound of claim 1, or a pharmaceutically acceptable salt thereof, wherein R$^1$ is C$_{1-6}$alkyl.

8. The compound of claim 7, or a pharmaceutically acceptable salt thereof, wherein R$^1$ is —CH$_3$.

9. The compound of claim 1, or a pharmaceutically acceptable salt thereof, wherein R$^2$ is hydrogen.

10. The compound of claim 1, or a pharmaceutically acceptable salt thereof, wherein R$^2$ is C$_{1-6}$alkyl.

11. The compound of claim 10, or a pharmaceutically acceptable salt thereof, wherein R$^2$ is —CH$_3$ or —CH$_2$CH$_3$.

12. The compound of claim 1, or a pharmaceutically acceptable salt thereof, wherein R$^3$ is C$_{3-6}$cycloalkyl or substituted C$_{3-6}$cycloalkyl.

13. The compound of claim 1, or a pharmaceutically acceptable salt thereof, wherein R$^3$ is C$_{1-6}$alkyl or substituted C$_{1-6}$alkyl.

14. The compound of claim 1, or a pharmaceutically acceptable salt thereof, wherein R$^3$ is cyclopropyl.

15. The compound of claim 1, or a pharmaceutically acceptable salt thereof, wherein R$^4$ is substituted phenyl.

16. The compound of claim 15, or a pharmaceutically acceptable salt thereof, wherein R$^4$ is halo substituted phenyl.

17. The compound of claim 16, or a pharmaceutically acceptable salt thereof, wherein R$^4$ is para-halo substituted phenyl.

18. The compound of claim 17, or a pharmaceutically acceptable salt thereof, wherein R$^4$ is para-chloro substituted phenyl.

19. The compound of claim 1, or a pharmaceutically acceptable salt thereof, wherein R$^5$ is substituted phenyl.

20. The compound of claim 19, or a pharmaceutically acceptable salt thereof, wherein R$^5$ is halo substituted phenyl.

21. The compound of claim 20, or a pharmaceutically acceptable salt thereof, wherein R$^5$ is meta-halo phenyl.

22. The compound of claim 21, or a pharmaceutically acceptable salt thereof, wherein R$^5$ is meta-chloro phenyl.

23. The compound of claim 1, or a pharmaceutically acceptable salt thereof, wherein n is 1.

24. The compound of claim 1, or a pharmaceutically acceptable salt thereof, wherein n is 0.

25. The compound of claim 1, or a pharmaceutically acceptable salt thereof, wherein A is a 5 membered heteroaryl group.

26. The compound of claim 1, or a pharmaceutically acceptable salt thereof, wherein A is a 6 membered heteroaryl group.

27. The compound of claim 26, or a pharmaceutically acceptable salt thereof, wherein A is pyridyl.

28. The compound of claim 1, or a pharmaceutically acceptable salt thereof, wherein A is pyridine-N-oxide.

29. The compound of claim 25, or a pharmaceutically acceptable salt thereof, wherein A is a thiazolyl group.

30. The compound of claim 1, or a pharmaceutically acceptable salt thereof, wherein R$^a$ is hydrogen.

31. The compound of claim 1, or a pharmaceutically acceptable salt thereof, wherein R$^a$ is C$_{1-6}$alkyl.

32. The compound of claim 1, or a pharmaceutically acceptable salt thereof, wherein:
X is S(=O)$_2$;
A is pyridyl or thiazolyl;
R$^1$ is C$_{1-6}$alkyl or hydrogen;
R$^2$ is hydrogen or C$_{1-6}$alkyl;
R$^3$ is C$_{3-6}$cycloalkyl or C$_{1-6}$alkyl;
R$^4$ is a phenyl or pyridyl group which is substituted with from one to three substituents independently selected from halo;
R$^5$ is a phenyl or pyridyl group which is substituted with from one to three substituents independently selected from halo; and
m is 1.

33. The compound of claim 1, or a pharmaceutically acceptable salt thereof, wherein:
X is S(═O)₂;
A is

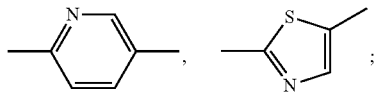

R¹ is —CH₃ or hydrogen;
R² is hydrogen;
R³ is cyclopropyl;
R⁴ is 4-chlorophenyl;
R⁵ is 3-chlorophenyl; and
m is 1.

34. The compound of claim 1, or a pharmaceutically acceptable salt thereof, selected from:
- 6-(((2S,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)methyl)nicotinic acid;
- 6-(((2R,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)methyl)nicotinic acid;
- 2-(((2R,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)methyl)-5-carboxypyridine 1-oxide;
- 2-(((2S,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)methyl)-5-carboxypyridine 1-oxide;
- 2-(((2R,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)thiazole-5-carboxylic acid;
- 2-(((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)thiazole-5-carboxylic acid;
- 6-(((2R,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)nicotinic acid; or
- 6-(((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)methyl)nicotinic acid.

35. A pharmaceutical composition comprising a compound of claim 1 or 34, or a pharmaceutically acceptable salt thereof, and a pharmaceutically acceptable excipient.

36. The compound of claim 1, or a pharmaceutically acceptable salt thereof, wherein Z is $C_{1-6}$alkyl.

37. The compound of claim 1, or a pharmaceutically acceptable salt thereof, wherein Z is $C_{3-6}$cycloalkyl.

* * * * *